(12) United States Patent
Gizzatov et al.

(10) Patent No.: US 11,808,146 B2
(45) Date of Patent: Nov. 7, 2023

(54) APPARATUS AND METHOD FOR OBSERVING PERFORMANCE OF A TREATMENT FLUID IN A CORE SAMPLE

(71) Applicant: ARAMCO SERVICES COMPANY, Houston, TX (US)

(72) Inventors: Ayrat Gizzatov, Cambridge, MA (US); Karim Ismail, Houston, TX (US); Mohammed Sayed, Houston, TX (US); Amy J. Cairns, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 262 days.

(21) Appl. No.: 17/157,256

(22) Filed: Jan. 25, 2021

(65) Prior Publication Data
US 2022/0235655 A1 Jul. 28, 2022

(51) Int. Cl.
*E21B 49/00* (2006.01)
*E21B 49/06* (2006.01)
*G01N 33/24* (2006.01)

(52) U.S. Cl.
CPC ............ *E21B 49/005* (2013.01); *E21B 49/06* (2013.01); *G01N 33/241* (2013.01)

(58) Field of Classification Search
CPC .......................... E21B 49/005; G01N 33/241
See application file for complete search history.

(56) References Cited

U.S. PATENT DOCUMENTS 4,149,804 A * 4/1979 Chew, III .............. E21B 49/005
356/416

4,640,140 A * 2/1987 Burghoffer ......... G01N 15/0255
73/863.22

(Continued)

FOREIGN PATENT DOCUMENTS

CN 108645999 A 10/2018
CN 110208265 A 9/2019
(Continued)

OTHER PUBLICATIONS

International Search Report and Written Opinion issued in Application No. PCT/US2022/013667, dated May 2, 2022 (14 pages).
N. S. K. Gunda et al.; "Reservoir-on-a-Chip (ROC): A new paradigm in reservoir engineering", Lab on a Chip; vol. 11; No. 22; Jan. 1, 2011 (9 pages).

(Continued)

*Primary Examiner* — John Fitzgerald
(74) *Attorney, Agent, or Firm* — Osha Bergman Watanabe & Burton LLP

(57) ABSTRACT

Testing apparatuses and their methods of use for testing core samples with treatment fluids, such as reactive fluids, such as acidic fluids, are provided. The testing apparatuses include a top and a base housing coupled together having a sample recess, a viewing window, and a primary distribution hole. Within the sample recess a core sample assembly is secured and immobilized. The core sample assembly in the testing apparatus is viewable through the viewing window and fluidly accessible through the primary distribution hole. Optionally, a light connector coupled to the testing apparatus provides light into the core sample assembly. Methods of using the testing apparatus include providing a testing apparatus with a core sample assembly secured and immobilized within the sample recess of the testing apparatus, introducing a treatment fluid to the core sample, and detecting the interaction within the testing apparatus of the core sample with the treatment fluid.

20 Claims, 19 Drawing Sheets

(56) References Cited

U.S. PATENT DOCUMENTS

| | | | | |
|---|---|---|---|---|
| 5,463,223 | A | * | 10/1995 | Wong ................. G01N 21/3563 250/339.08 |
| 5,493,226 | A | | 2/1996 | Honarpour et al. |
| 6,194,160 | B1 | * | 2/2001 | Levin ..................... B01F 31/23 435/7.1 |
| 6,200,531 | B1 | * | 3/2001 | Liljestrand ............. G01N 21/69 250/361 C |
| 8,863,567 | B2 | * | 10/2014 | Jappy .................... E21B 21/003 73/61.64 |
| 10,302,544 | B2 | * | 5/2019 | Drake ..................... E21B 43/26 |
| 10,373,800 | B2 | * | 8/2019 | Gardiner .................. B01L 9/52 |
| 10,466,153 | B2 | * | 11/2019 | Gupta ................ G01N 15/0826 |
| 10,844,711 | B2 | * | 11/2020 | Cooper ................... E21B 49/02 |
| 11,148,137 | B2 | * | 10/2021 | Wang ............... B01L 3/502707 |
| 2008/0194426 | A1 | | 8/2008 | Goodman et al. |
| 2012/0211162 | A1 | | 8/2012 | Ellis |
| 2016/0123890 | A1 | * | 5/2016 | He ........................ G01N 21/84 73/53.01 |
| 2017/0098526 | A1 | * | 4/2017 | Gardiner .................. B01L 9/52 |

FOREIGN PATENT DOCUMENTS

| | | | |
|---|---|---|---|
| CN | 110671090 A | | 1/2020 |
| KR | 2015041834 A | * | 4/2015 |

OTHER PUBLICATIONS

T. Jacobs; "Reservoir-on-a-Chip Technology Opens a New Window Into Oilfield Chemistry", Journal of Petroleum Technology; Dec. 31, 2018 (3 pages).

W. Yun et al.; "Toward Reservoir-on-a-Chip: Rapid Performance Evaluation of Enhanced Oil Recovery Surfactants for Carbonate Reservoirs Using a Calcite-Coated Micromodel", Scientific Reports; vol. 10; No. 1; Dec. 2020 (12 pages).

T. W. de Haas et al.; "Steam-on-a-chip for oil recovery: the role of alkaline additives in steam assisted gravity drainage", Lab on a Chip; vol. 13; No. 19; Jan. 2013 (9 pages).

Gerold, Chase T. et al., "Microfluidic devices containing thin rock sections for oil recovery studies", Microfluidics and Nanofluidics, Springer-Verlag GmbH, vol. 22, No. 76, Jul. 2018, pp. 1-7 (7 pages).

* cited by examiner

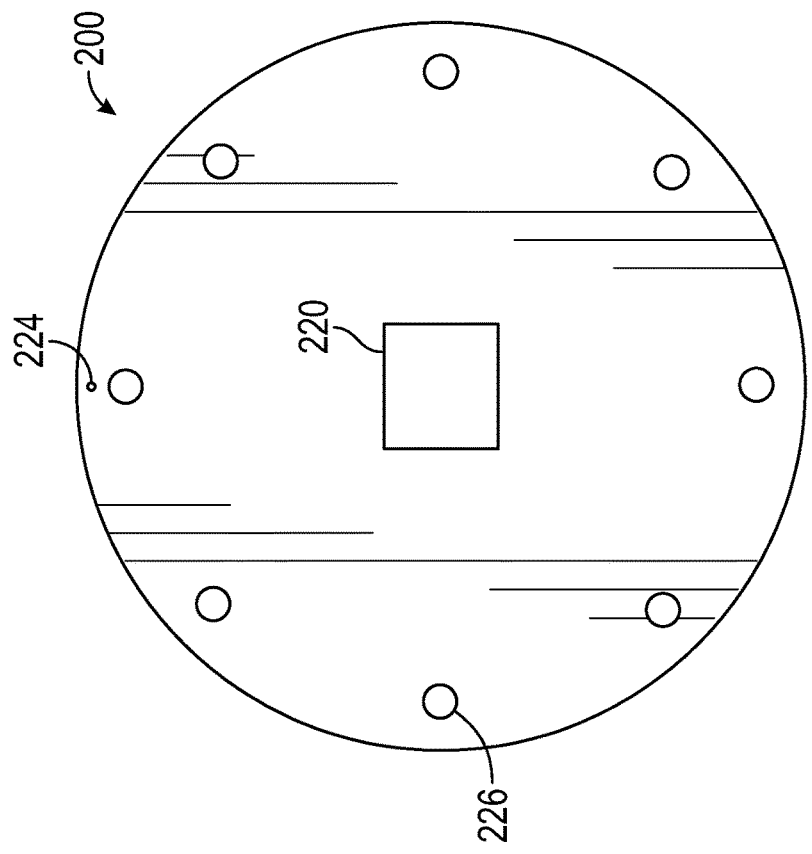
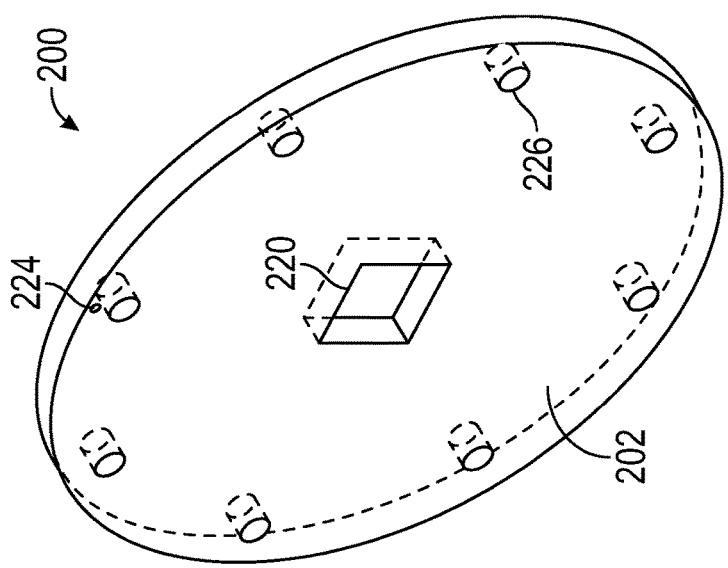
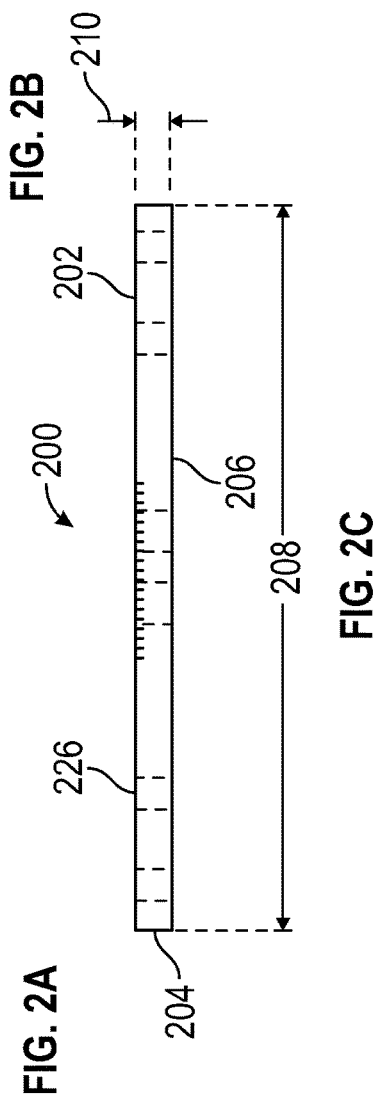
FIG. 2B
FIG. 2C
FIG. 2A

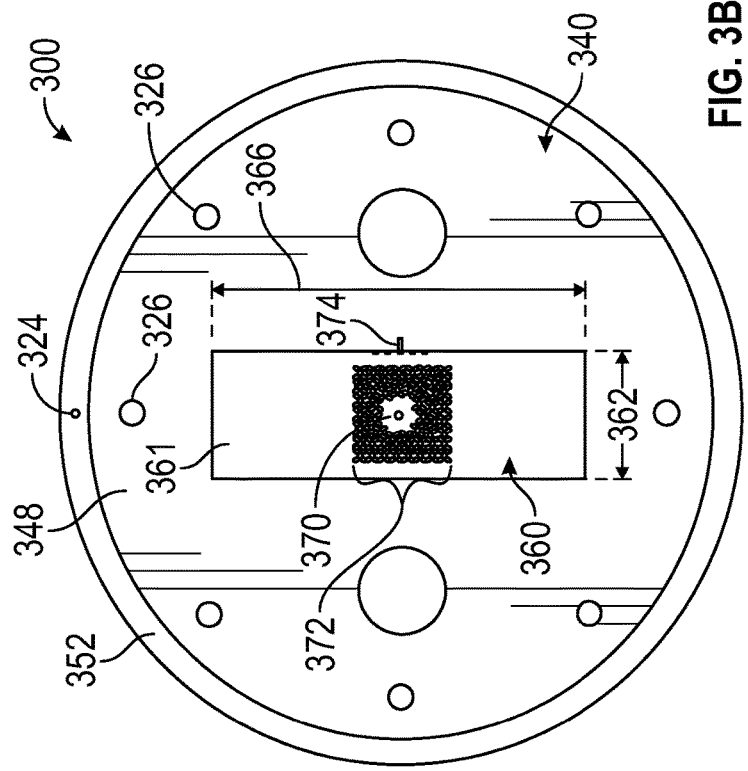
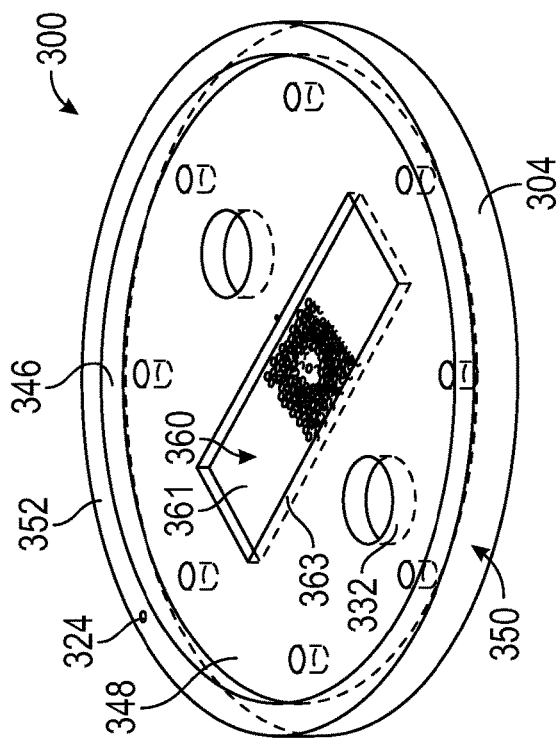
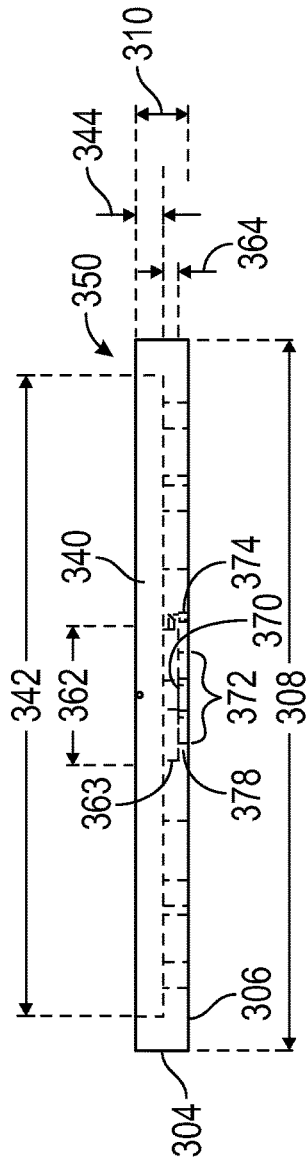
FIG. 3B
FIG. 3A
FIG. 3C

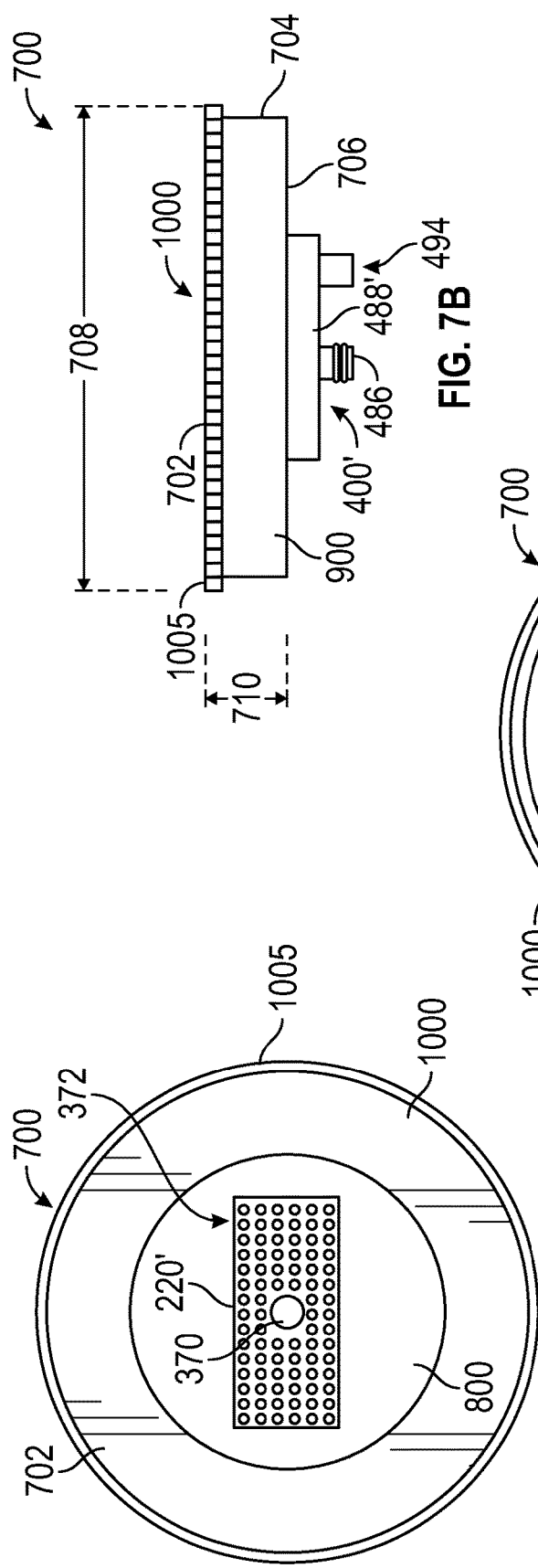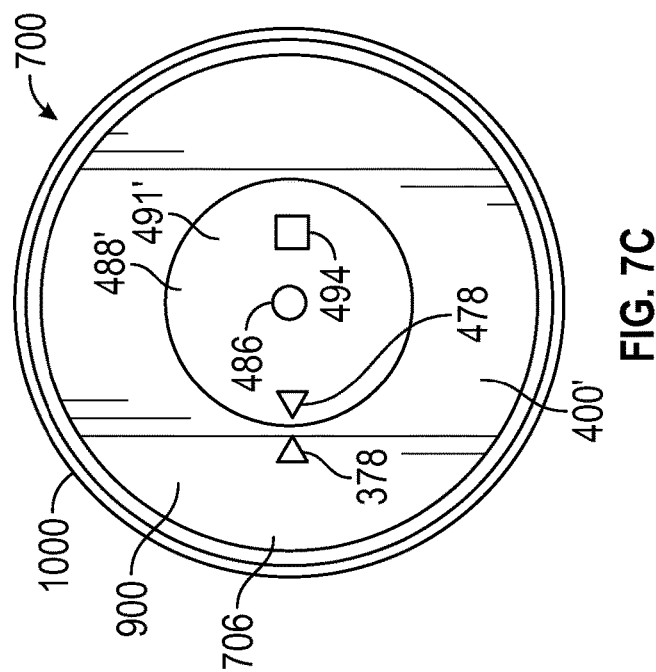

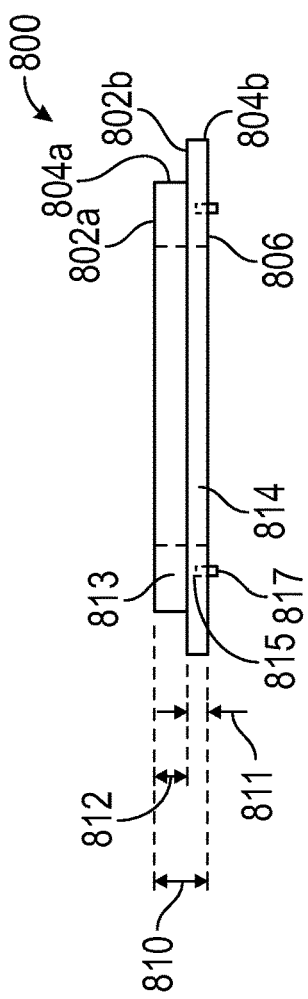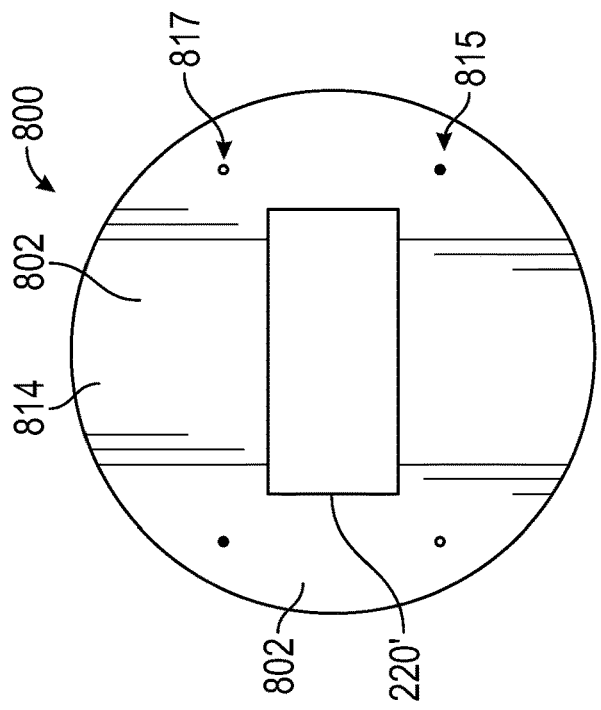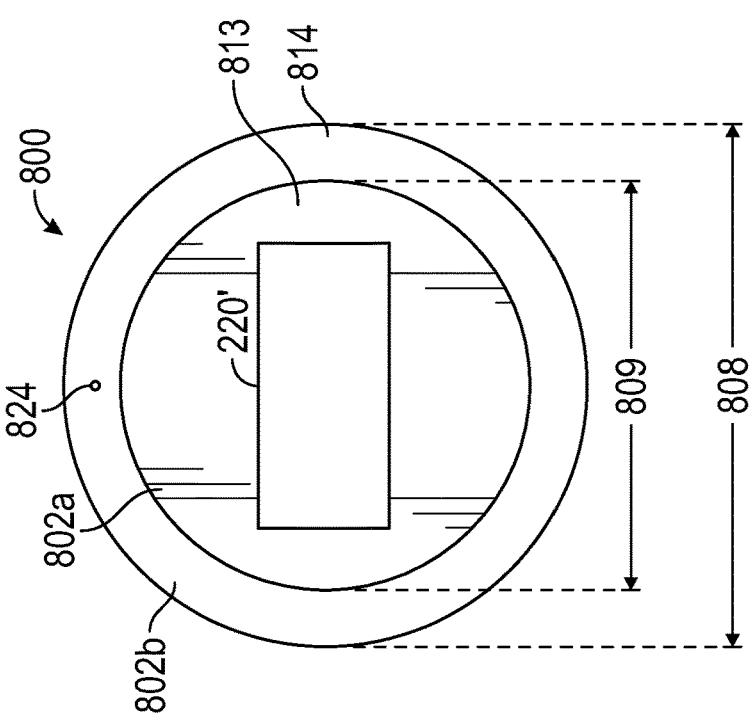

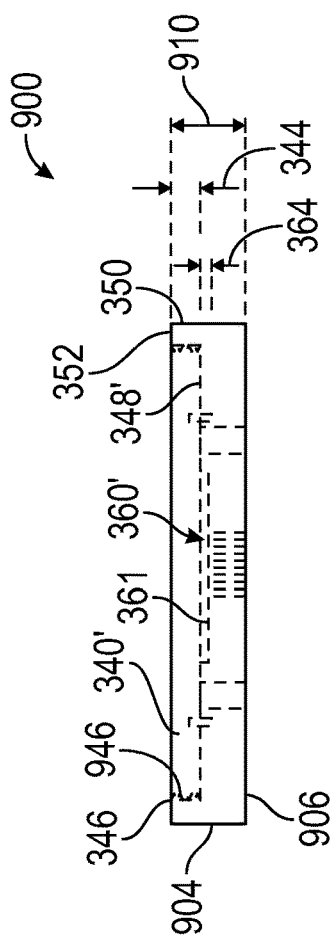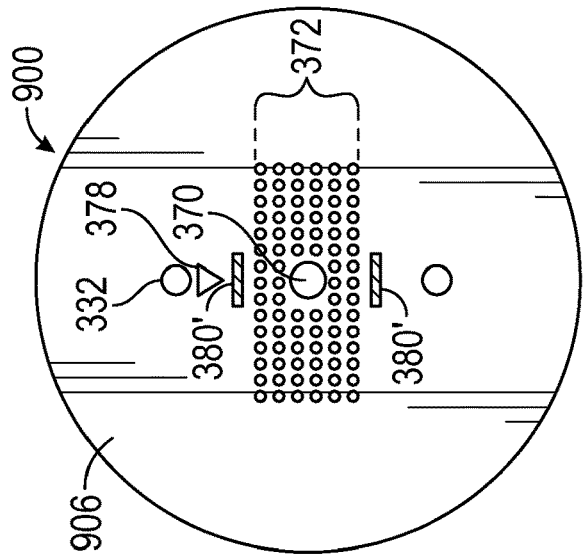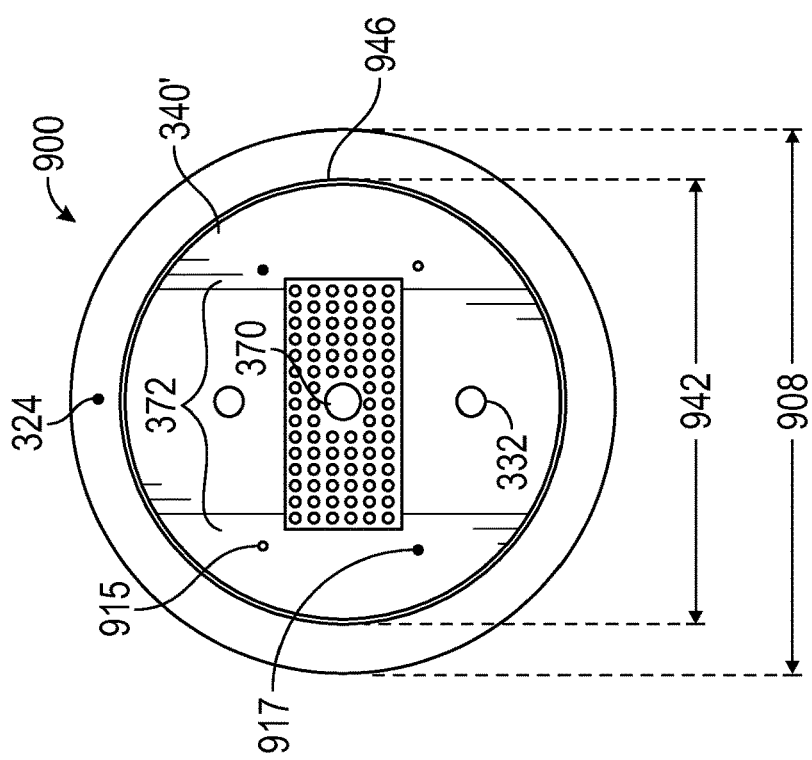

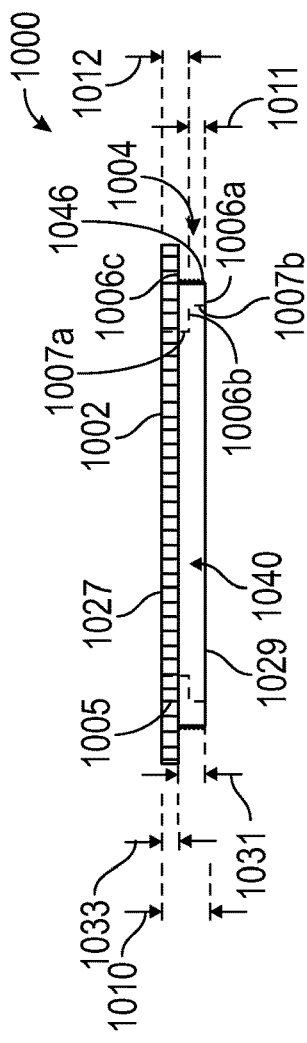
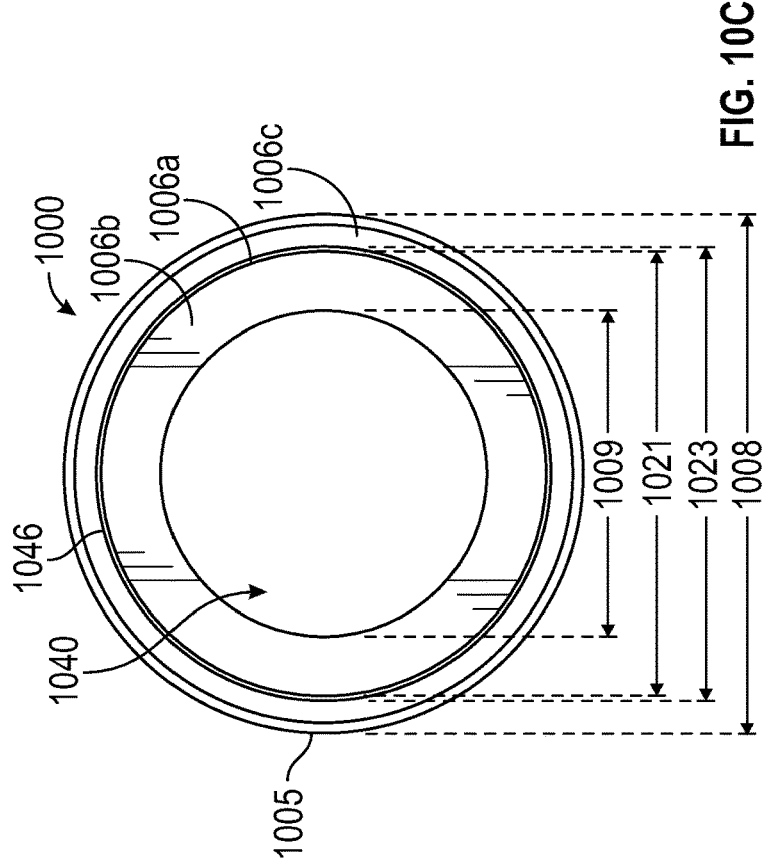
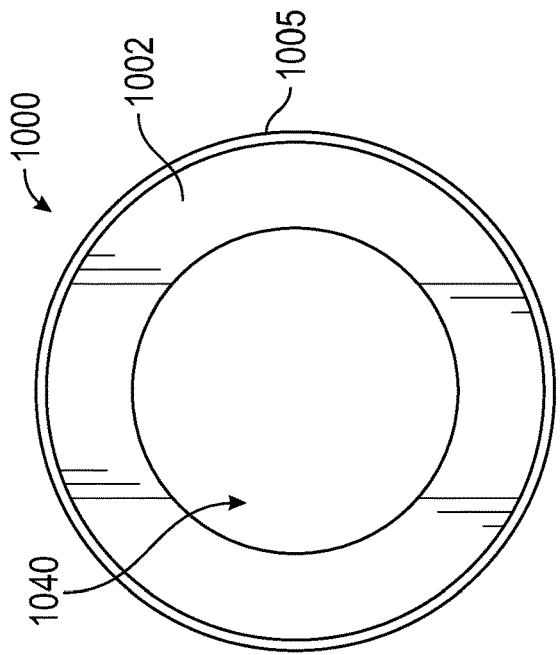
FIG. 10B
FIG. 10C
FIG. 10A

APPARATUS AND METHOD FOR OBSERVING PERFORMANCE OF A TREATMENT FLUID IN A CORE SAMPLE

BACKGROUND

In the field of oil and gas production, the delivery of treatment fluids, such as reactive fluids, and such as acidic fluids especially, to not only a remote location, but also, within a formation downhole provides a myriad of logistical and technical problems and solutions. Treatment fluid systems are used for a variety of reasons, including to create improved flow paths for oil or gas recovery. Using acid systems can permit the formation of wormholes via dissolution of formation matrix near the wellbore, for example, in a well that is damaged due to the drilling process. Treatment fluids may be used in large quantities, the volume of which is dependent on the nature of the operation. For example, a matrix acidizing treatment or acid fracturing treatment of a single stage of a multistage vertical or horizontal well may require significant volumes of treatment fluid. Testing that may provide any insight into the handling, use or even alternatives to hazardous, toxic, reactive, or expensive/rare chemicals is valuable information to those in the field.

SUMMARY

The foregoing general description and the following detailed description are exemplary and are intended to provide an overview or framework for understanding the nature of what is claimed.

Embodiment testing apparatuses may include a top housing that is coupled to a front side of a base housing. In so coupling, a surface-surface contact forms between the top housing and the base housing. The testing apparatus has a sample viewing window that is paneless. The testing apparatus has a sample recess, which is defined by the front side of the base housing, that is configured to receive a core sample assembly. The sample recess is configured such that the position of the core sample assembly within the testing apparatus is directly observable through the sample viewing window. The testing apparatus has a primary distribution hole that permits direct fluid access to a core sample, which is part of the core sample assembly, within the sample recess. The core sample assembly is secured and immobile when the top housing is coupled to the bottom housing. A surface-surface contact is formed between the lower surface of the core sample assembly and the front side of the base housing. Optionally, a light connector is coupled to a back side of the case housing. In such instances, a surface-surface contact forms between the base housing and the light connector.

Embodiment methods of testing a core sample using the previously described testing apparatus may include providing the previously described testing apparatus with a core sample assembly secured and immobile within the testing apparatus. The core sample assembly is viewable through the sample viewing window. The methods include introducing a treatment fluid into the testing apparatus. The treatment fluid is introduced such that that it passes through the primary fluid distribution hole and interacts with the core sample. The methods include detecting the interaction within the testing apparatus between the treatment fluid and the core sample.

BRIEF DESCRIPTION OF DRAWINGS

The following is a description of the figures in the accompanying drawings. The accompanying drawings are included to provide further understanding and are incorporated in and constitute a part of the specification. The drawings illustrate various embodiments and together with the description explain principles and operations of an apparatus and system useful for evaluating fluids both reactive and non-reactive through a sample of formation material.

FIGS. 2A-C show the top housing in perspective, front, and side views according to one or more embodiments of the testing apparatus 100.

FIGS. 3A-D show the base housing in perspective, front, side and back view according to one or more embodiments of the testing apparatus 100.

FIGS. 6C-1-3 shows a side view of a second example core sample assembly, and the upper surface and the lower surface of said core sample assembly.

FIGS. 7A-C show an assembled testing apparatus in front, side, and back views according to one or more embodiments.

FIGS. 8A-C show the yoke in front, side, and back view according to one or more embodiments of the testing apparatus 700.

FIGS. 9A-C show the base housing in front, side, and back view according to one or more embodiments of the testing apparatus 700.

FIGS. 10A-C show the top housing in front, side, and back views according to one or more embodiments of the testing apparatus 700.

Figure 1A:
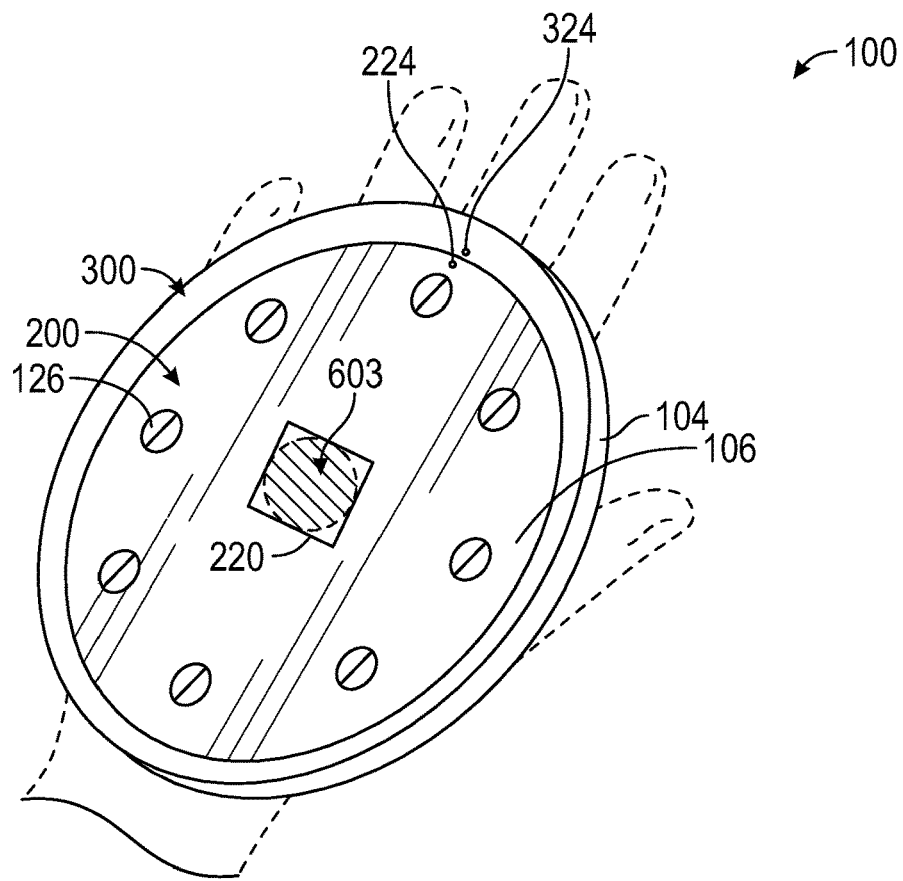
FIGS. 1A-B show an assembled embodiment testing apparatus in perspective and side view according to one or more embodiments.

For the sake of continuity, and in the interest of conciseness, the same or similar reference characters may be used for same or similar objects in multiple figures. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the shapes of the elements as drawn are not necessarily intended to convey any information regarding the actual shape of the elements and have been selected for ease of recognition in the drawing.

DETAILED DESCRIPTION

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth.

Evaluating the relative performance of a fluid used in the field, such as a treatment fluid, such as a reactive fluid system, such as an acidic fluid, in laboratory scale testing still has traditionally had similar handling issues. Using full-sized core samples is not effective means to perform screening tests on new materials. Laboratory tests commonly rely on the use of core flow measurements to evaluate the acidizing performance of a reactive fluid. Data such as pore volume to breakthrough and visual representations of wormhole characteristics are needed. To visualize wormholes, though, usually a computer-tomography (CT) image is needed. This is an off-line test—it cannot be obtained during the application of the acid medium. As well, it is nearly impossible to observe the results of the acidification visually in "real time". Other problems in using whole core samples include physically handling the cores themselves. Core samples are heavy, awkward to handle, and contain a lot of material that is difficult to obtain and is in high demand of many scientists, engineers, geologists, and researchers. Regarding the difficulty to obtain the core sample material, the issue of scarcity is especially true if the laboratory is supporting a site where active drilling or production is occurring thousands of miles away. Finally, the hazards of handling and using quantities of materials that are in proportion to the core sample may lead to the use and exposure of lab personnel to the same safety concerns that are in the field for applying reactive, acidic, toxic, or expensive chemical packages to the core samples.

A useful testing apparatus and its method of use would provide a way to permit the reduction of the sample size of the core material to preserve scarce resources. Such an apparatus and method of use would also result in reducing the amount of treatment fluid applied to such core material samples, which would not only reduce waste from excessive chemical use but also reduce the hazards of using such chemicals by reducing their overall quantities handled by a researcher. Reducing sample size would also avoid any issues with handling whole cores, including injury, logistics, and downtime. A useful testing apparatus and its method of use would permit direct observation of the interaction of the treatment fluid with the core sample so that a real-time assessment could be made for the viability of using the treatment fluid with the formation material. A useful testing apparatus would be made of only several parts. A useful testing apparatus would be relatively easy to assemble, use, disassemble, and clean so that a number of samples or treatment fluids may be rapidly tested in succession to determine potential solutions for issues confronting the field. A useful testing apparatus may be of a hand-held size and possibly light enough that the device may be held in hand while a test is performed. Embodiment testing apparatuses and methods of their use provide such advantages and more.

In some implementations, an embodiment testing apparatus may allow for observation and memorialization of the behavior and reactivity of treatment fluids, such as a reactive fluid, such as an acidic fluid, propagating into and through a core sample in real-time. "Real-time" means as it relates to an observer, whether it is a person, a computer, or an object acting as a means for detecting a change, such as a sensor, some or all, that the observer is capable using the embodiment device to monitor the initiation of treatment and witness a change in configuration to the core sample, if any, from before the introduction of the treatment fluid, during the introduction of the treatment fluid, and through the conclusion of the introduction of the treatment fluid or the cessation of observation, whichever occurs first, as the events occur and without delay. For example, using an embodiment testing apparatus, an observer may witness through the sample viewing window the introduction of a treatment fluid that is an acidic fluid into the core sample and the resultant impact on the core sample matrix, such as etching, reactivity, or dissolution of matrix material. There is no effective delay for the observer between performing the introduction action and the ability to obtain visual or optical information on the result of that action due to the configuration of the embodiment testing apparatus. With such near-instantaneous results, laboratory personnel can make quick decisions regarding scaling up testing, modifying testing programs, or report initial trial results to the field for their information and possible action.

Embodiment testing apparatuses and the methods of use effectively promote the use of a "reservoir on a chip" type of testing. Small amounts of synthetic or real formation material, such as samples of recovered core materials or slices of core plugs may be used to run experiments with the intention of application to the field. Attempts using a testing apparatus may be made to simulate on a microscale-sized core sample (that is, several millimeters to several inches in width or diameter) the fluid behavior and interaction that occurs within a vast formation or reservoir comprised of the same material. Testing both simulated and actual formation materials aids in the development of treatment fluids, especially reactive fluids, such as acidic fluids, for use in in the field on similar or the same formation compositions.

Embodiment testing apparatuses and the methods of use facilitate the safe handling and effective use of scarce resources, like core materials. Embodiment testing apparatuses, such as those of a hand-held size, only use several cubic centimeters of formation material per test. This preserves hard-to-obtain samples material for additional research or preservation, benefiting other researchers as well as reducing requests to the field to recover such materials, which may be bothersome to production operations.

In using reduced sample sizes, the amount of chemicals, including potentially toxic or life-threatening materials, is reduced significantly versus the amounts required to test whole core samples. Being able to perform screening tests using small portions of chemicals reduces risks for researchers that may be using unfamiliar materials, such as a new composition. Smaller portions also result in smaller amounts of waste of which to dispose.

Embodiment testing apparatuses are only made of a few components, the two largest being a bottom housing and a top housing that couple together. This simple design results in a testing apparatus that is easy to assemble, use, disassemble, and clean. In combination with the small samples and the quantity of chemicals, the use and maintenance of the apparatus may be relatively easier and lead to an increased turnover rate of experiments using the same apparatus.

Unlike other testing apparatuses, embodiment testing apparatuses provide the ability to directly observe interaction between a treatment fluid and the core sample. Based upon the configuration of the core sample assembly in relation to the top housing, a sample viewing window in the top housing affords easy visual and physical access to the core sample assembly while positioned within the testing apparatus. There is no requirement for the sample viewing window to have viewing surface pane, such as one made of glass or plastic, between the observer and the core sample apparatus. Rather, viewing at least a portion of the core sample assembly is unrestricted. This is possible because of the surface-surface contact between the upper surface and the core sample in the core sample assembly that not only prevent fluid bypass of the core sample, but also, shields the observer from exposure to the treatment fluid. This unobstructed view of the core sample, such as by a person or a device using recording media, to study or optionally memorialize the performance of the treatment fluid interacting with the core sample, permits direct and immediate observation of the treatment fluid with the core sample.

First Embodiment Testing Apparatus

Figure 1B:
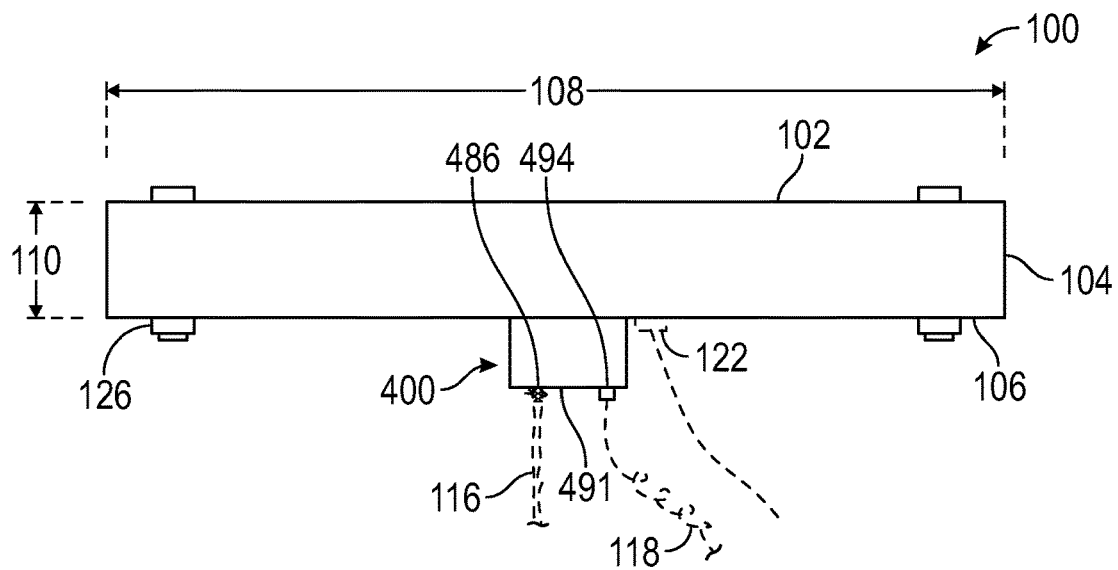

FIGS. 1A and 1B show an assembled embodiment testing apparatus in perspective and side view according to one or more embodiments. Testing apparatus 100 has an apparatus front surface 102, an apparatus side edge 104, and an apparatus back surface 106. Embodiments of the testing apparatus 100 include several exterior-observable components that are coupled, including top housing 200, base housing 300, and optional light connector 400.

Observable from perspective view FIG. 1A are several features of embodiment testing apparatus 100. Fasteners 126 may couple the top housing 200 to the base housing 300. There are also associated top housing alignment mark 224 and first base housing alignment mark 324 that appears generally aligned. Sample viewing window 220 is defined by top housing 200, permitting observation of a core sample 603 (in relief) positioned within testing apparatus 100. These and other attributes of the embodiment testing apparatus 100 will be described in more detail.

FIG. 1B shows optional light connector 400 coupled to base housing 300 along the apparatus back surface 106 using a second coupling means, which will be described. Coupled to light connector 400 via light connector fluid connector 486 is primary fluid conduit 116 (in relief). Coupled to light connector 400 via light connector power connector 494 is power conduit 118 (in relief). Optionally, a secondary fluid conduit 122 (shown in relief) is coupled to the testing apparatus 100 along the apparatus back surface 106 at some space from light connector 400.

In FIG. 1A, the embodiment testing apparatus 100 appears as if resting in the palm of a human hand shown in relief. Although embodiment apparatus 100 may take any general form and size, testing apparatus 100 may have an apparatus diameter 108 and an apparatus thickness 110 in some embodiments that are appropriate for a hand-held sized testing apparatus.

FIGS. 2A-C show the top housing in perspective, front, and side views according to one or more embodiments of the testing apparatus 100. Top housing 200 has a top housing front surface 202, a top housing side edge 204, and a top housing back surface 206. Top housing front surface 202 comprises part of apparatus front surface 102.

Top housing 200 is also shown to have a top housing thickness 210 and a top housing diameter 208. For testing apparatus 100, top housing thickness 210 is less than apparatus thickness 110, and top housing diameter 208 is less than apparatus diameter 108.

FIGS. 2A-B also shows top housing alignment mark 224 on top housing front surface 202 and sample viewing window 220, as previously described. Embodiment testing apparatus have a "paneless" sample viewing window. That is, the sample viewing window 220 does not have a pane; that is, there is no transparent surface, such as glass or plastic, traversing that is traversing the void of the sample viewing window. Sample viewing window 220 traverses through a top housing thickness 210 and provides an unobstructed view of the interior of testing apparatus, such as into sample recess 360. The configuration of sample viewing window 220 is shown in FIG. 2A is being approximately square; however, instances of the sample viewing window 220 are not so limited.

In some other embodiments, the space defined by sample viewing window is occupied by a transparent material, such as glass or plastic.

In some embodiment, the top housing alignment mark 224 may be formed of a material subject to magnetism or a magnetic material, that is, a material that is operable to induce a magnetic effect, such as attraction or repulsion, in a material subject to magnetism.

In addition, FIGS. 2A-C show one or more fastener holes 226 formed in top housing 200. Fastener holes 226 are disposed in a radial pattern around a center of the top housing 200, although one of ordinary skill in the art may select another appropriate pattern for applying equilateral sealing pressure. Fastener holes 226 are configured for embodiment testing apparatus 100 to permit a portion of fasteners 126 to pass through the top housing 200.

Figure 3D:
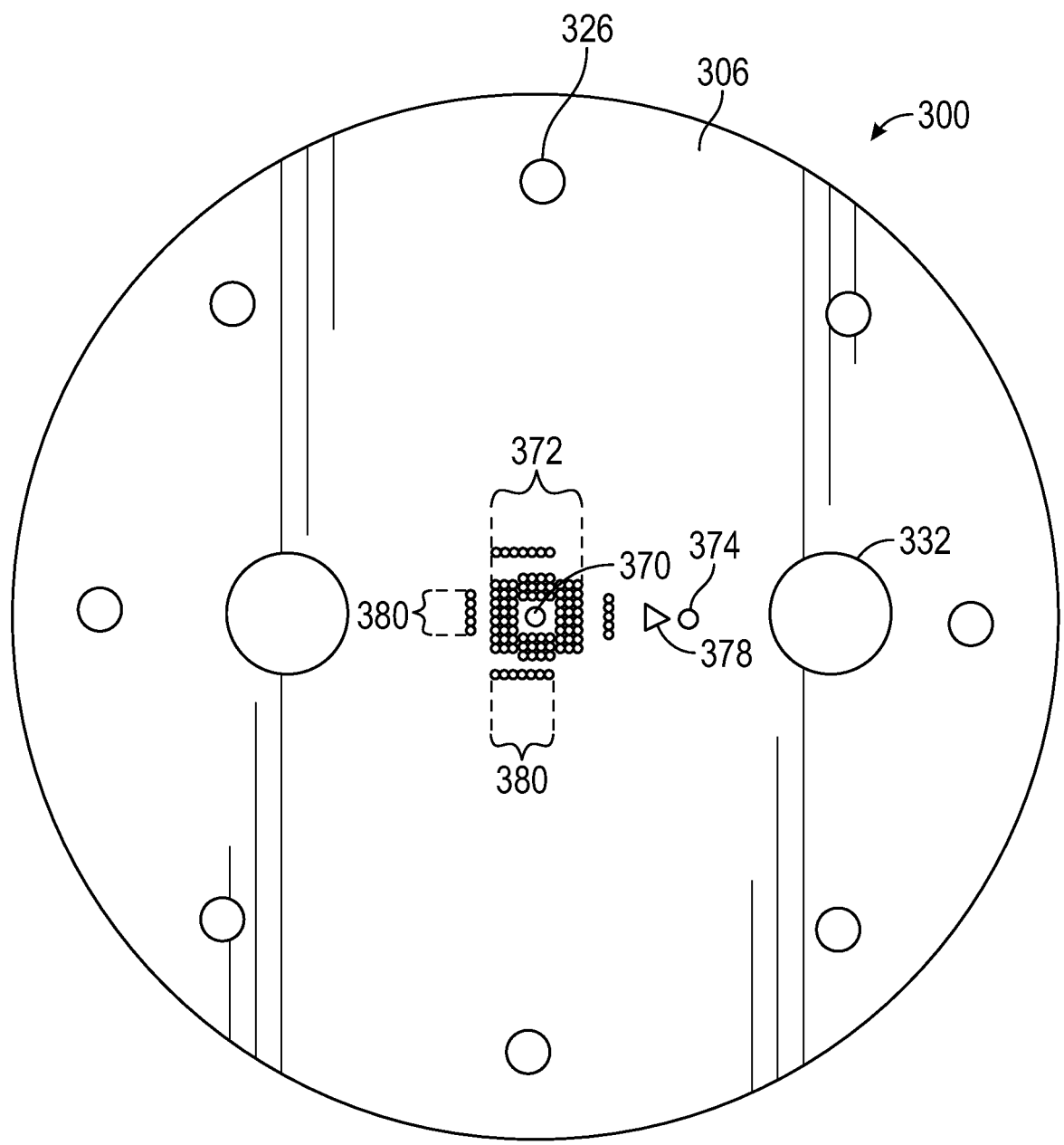

FIGS. 3A-D show the base housing in perspective, front, side, and back views according to one or more embodiments of the testing apparatus 100. Base housing 300 has a base housing side edge 304 and a base housing back surface 306. Base housing side edge 304 comprises apparatus side edge 104. Base housing back surface 306 comprises apparatus back surface 106. Base housing 300 has several front-facing surfaces. The front edge 352 of base lip 350, top housing recess front surface 348, and sample recess front surface 361 all combine to provide the front-facing surfaces of base housing 300, as seen in FIG. 3B.

Base housing 300 along its exterior surface has a base housing thickness 310 and a base housing diameter 308. For embodiment testing apparatus 100, base housing thickness 310 is the apparatus thickness 110, and base housing diameter 308 is the apparatus diameter 108.

Base housing 300 of embodiment testing apparatus 100 includes several recesses, such as top housing recess 340. Top housing recess 340 is configured such that top housing 200 may be introduced into top housing recess 340. Top housing recess 340 is defined in base housing 300 by top housing recess diameter 342 and top housing recess depth 344. In some embodiments, the top housing recess diameter 342 is approximately the same as the top housing diameter 208. In some embodiments, the top housing recess depth 344 is approximately the same as top housing thickness 210. Top housing recess 340 is bound by the top housing recess edge 346 of base lip 350 and top housing recess front surface 348.

The testing apparatus is configured with a sample recess 360 in base housing 300. Sample recess 360 is configured to accept and retain a core sample assembly for testing in testing apparatus 100. Sample recess 360 is positioned relative to top housing recess 340 such that when top housing 200 is in position within top housing recess 340, sample recess 360 forms a defined, fixed volume within base housing 300 for a core sample assembly 601 to occupy. Although the volume of sample recess may take any variation, in the embodiment testing apparatus 100, sample recess 360 is defined in base housing 300 to have sample recess width 362, sample recess depth 364, and sample recess length 366. Sample recess 360 is bound by the sample recess edge 363 and sample recess front surface 361.

Base housing 300 of embodiment testing apparatus may include several holes or conduits that traverse the base housing 300 from base housing back surface 306 to top housing recess front surface 348. In an embodiment of the testing apparatus 100, base housing 300 may define one or more release holes 332. The release hole 332 may be distributed in the portion of base housing 300 among top housing recess front surface 348. During coupling of the top housing with the base housing, the release hole 332 may permit trapped air to escape the embodiment apparatus 100. The release holes 332 may also be a means to uncouple the top housing 200 from the base housing 300 after the two housings 200, 300 have been mated.

Another set of holes defined in the portion of base housing 300 among top housing recess front surface 348 is one or more fastener holes 326. As seen in FIGS. 3A-D, fastener holes 326 are disposed in a radial pattern around a center of the base housing 300, although one of ordinary skill in the art may select another appropriate pattern for applying equilateral sealing pressure. Fastener holes 326 are configured for embodiment testing apparatus 100 to permit a least a portion of fasteners 126 to pass through the base housing 300. In embodiments, the number and position of fastener holes 326 in base housing correspond with the number and position of fastener holes 226 in top housing 200.

In alternative embodiments, the fastener holes 326 do not fully pass through base housing 300 and out the base housing back surface 306. Rather, in such embodiments, fastener holes 326 are instead fastener stops. A fastener stop is understood to have a defined depth that is less than the thickness 310 of the base housing 300 minus the top housing recess depth 344, which in the portion of base housing 300 in the area having top housing recess front surface 348 is the thickness of base housing 300. In such instances, fastener stops may have counter-threads to any threads the fasteners 126 possess to engage fasteners 126 and halt the progress of the fasteners 126. The depth of the fastener stop may be related to preventing the over-torqueing of fasteners 126 and mitigation of potential damage to the core sample assembly position when testing apparatus 100 is fully assembled. As well, the lack of holes in base housing may also provide additional insurance of fluid containment within testing apparatus 100.

Base housing 300 of embodiment testing apparatus may include several holes or conduit that traverse the base housing 300 from base housing back surface 306 to sample recess 360. In an embodiment of the testing apparatus, base housing 300 may define one or more light distribution holes 372. As shown in FIGS. 3A-D, light distribution holes 372 are positioned as a cluster in the center of base housing 300 and traverses into sample recess 360; however, this configuration is not required. Light distribution holes 372 permit the transmission of artificial light or other electromagnetic energy (EM) from optional light connector 400, through base housing 300, and into sample recess 360. In some embodiments of the testing apparatus 100, the position of the light distribution holes 372 in base housing 300 is configured such that light distribution holes 372 are associated with the position of sample viewing window 220 when top housing 200 coupled with base housing 300, although it is understood that this is not necessarily required.

Testing apparatus is configured with a primary fluid distribution hole, defined in the portion of base housing 300 among sample recess 360. As shown in FIGS. 3A-D, primary fluid distribution hole 370 is positioned in the center of base housing 300; however, this is not required. In FIGS. 3A and D, light distribution holes 372 are configured to surround primary fluid distribution hole 370. Again, this is not required for embodiments of the testing apparatus. Primary fluid distribution hole 370 permits the conveyance of a treatment fluid, such as reactive fluid, such as an acidic fluid, from optional light connector 400 (or a non-pictured optional removable fluid connector), through base housing 300, and into sample recess 360. In some embodiments of the testing apparatus 100, the position of primary fluid distribution hole 370 in base housing 300 is configured such that primary fluid distribution hole 370 is associated with the position of sample viewing window 220 when top housing 200 is coupled with base housing 300, although it is understood that this is not required.

Optionally, one or more additional holes may be defined in the portion of base housing 300 among sample recess 360. As shown in FIGS. 3A-B and D, there is a secondary fluid distribution hole 374 configured in the base housing 300. The secondary fluid distribution hole 374 is a fluid conduit that may convey both fluid and solids from the sample recess 360, through base housing 300, and out of the testing apparatus 100, such as by optional secondary fluid conduit 122 (such as shown in relief in FIG. 1B). An opening for secondary fluid distribution hole 374 in sample recess 360 is along sample recess edge 363 proximate to the cluster of light distribution holes 372. In other embodiments, there may be more than one secondary fluid distribution holes. In such embodiments, treatment fluid may flow from the primary fluid distribution hole 370 to the more than one secondary fluid distribution holes 374 and show interaction of treatment fluid, such as reactive fluid, such as acidic fluid, along multiple fluid flow paths to multiple exit points. Other combinations, configuration patterns, numbers, and uses of the primary fluid distribution hole 370 and the one or more secondary fluid distribution hole 374 in coordination with each other to produce fluid flow patterns within sample recess 360 are envisioned. In some embodiments of the testing apparatus 100, the position of secondary fluid distribution hole 374 in base housing 300 is configured such that secondary fluid distribution hole 374 is associated with the position of sample viewing window 220 when top housing 200 coupled with base housing 300, although it is understood that this is not required.

Optionally, and in association with the one or more secondary fluid distribution holes, embodiments of the testing apparatus may include a means for coupling one or more secondary fluid conduits 122 to base housing 300 via base housing back surface 306. In some embodiments of the testing apparatus 100, the coupling means is an extension of base housing, similar to such as light connector fluid connector 486 (FIG. 1B), or other known mechanical connections (for example, ¼ turn connector, clamp, twist tie). In some embodiments of the testing apparatus, a removable fluid connector may couple the secondary fluid conduits 122 to the base housing 300.

The removable fluid connector may be configured, for example, to frictionally couple with at least a portion of the interior of the secondary fluid distribution hole 374. Such a removable fluid connector may be made of a material that is resistant to the treatment fluid while retaining flexibility, such as a silicone. One of ordinary skill in the art may appreciate that fastening one or more secondary fluid conduits 122 to base housing 300 may take the form of any common connector for securing a fluid conduit, including such connectors as may be required for conveying a treatment fluid or its resultant fluid or slurry after interaction with the core sample at a pressure greater than atmospheric pressure, such as at wellbore pressure. In some embodiments, the coupling means may be done by a magnetic connection, such as where base housing 300 includes a material subject to magnetism or a magnetic material and the secondary fluid conduit 122 has an appropriately reciprocal coupling means. Other common coupling means for distributing treatment fluids, such as reactive fluids, such as acidic fluids, or receiving the effluent fluid or slurry of said fluids after interaction with a core sample, are understood within the art and envisioned.

FIGS. 3A-B also shows first base housing alignment mark 324 on front edge 352 of base lip 350. The first base housing alignment mark 324 is associated with the top housing alignment mark 224. The association of first base housing alignment mark 324 with top housing alignment mark 224 is such that the configuration of certain other elements of both top housing 200 and base housing 300 are aligned when top housing 200 in top housing recess 340 of base housing 300 and base housing are aligned. For example, top housing alignment mark 224 and first base housing alignment mark 324 may be configured such that when the two alignment marks 224, 324 are aligned, the fastener holes 226, 326 are aligned. In another example, the when the two alignment marks 224, 324 are aligned, the sample viewing window 220 may be aligned with light distribution holes 372 in sample recess 360.

In some embodiment, the first base housing alignment mark 324 may be formed of a material subject to magnetism or a magnetic material, as previously described. In such an embodiment, the use of a magnetic material is configured in testing apparatus 100 such that there is an attractive force that confirms alignment of top housing 200 with base housing 300. For example, top housing alignment mark 224 may comprise a magnetic material whereas first base housing alignment mark 324 may comprise a material subject to magnetism. In such an instance, when of top housing 200 is positioned within top housing recess 340 of base housing 300 and top housing alignment mark 224 is proximate to first base housing alignment mark 324, a magnetic force between the two alignment marks 224, 324 is induced that can be detected. Other variations between magnetic material and material subject to magnetism for guiding the positioning of top housing 200 within base housing 300 are envisioned.

FIG. 3D shows optional second base housing alignment mark 378 on base housing back surface 306. Second base housing alignment mark 378 is associated with optional light connector 400, as will be described. In some embodiment, the second base housing alignment mark 378 may be formed of a material subject to magnetism or a magnetic material, as previously described.

FIG. 3D also shows optional base housing magnetic coupling 380 on base housing back surface 306. Base housing magnetic coupling 380 is associated with optional light connector 400, as will be described. Base housing magnetic coupling 380 is formed of materials subject to magnetism, a magnetic material, or combinations thereof, as previously described.

As shown in FIG. 3D for embodiment of the testing apparatus 100, optional base housing magnetic coupling 380 may be configured in an asymmetric pattern, such as an asymmetric box-like pattern around a center of the base housing 300; however, other asymmetric and symmetric geometric patterns are envisioned. As well, the base housing magnetic coupling 380 may be configured in a regular or irregular distribution of its member elements along base housing back surface 306. FIG. 3D shows an example of this. Elements of base housing magnetic coupling 380 are distributed 5 elements stage right and left and 7 stage top and bottom around the cluster of light distribution holes 372. Other symmetrical or asymmetrical patterns are envisioned.

In some embodiments of the testing apparatus, such as testing apparatus 100, an optional, removable fluid connector may couple the primary fluid conduit 116 to the base housing 300. Such a connector may permit treatment fluid, such as a reactive fluid, such as an acidic fluid, to be conveyed to the core sample assembly in the sample recess 360 from the primary fluid conduit 116 without use of light connector 400. The removable fluid connector may be configured, for example, to frictionally couple with at least a portion of the interior of the primary fluid distribution hole 370. Such a removable fluid connector may be made of a material that is resistant to the treatment fluid while retaining flexibility, such as a silicone.

Figure 4C:
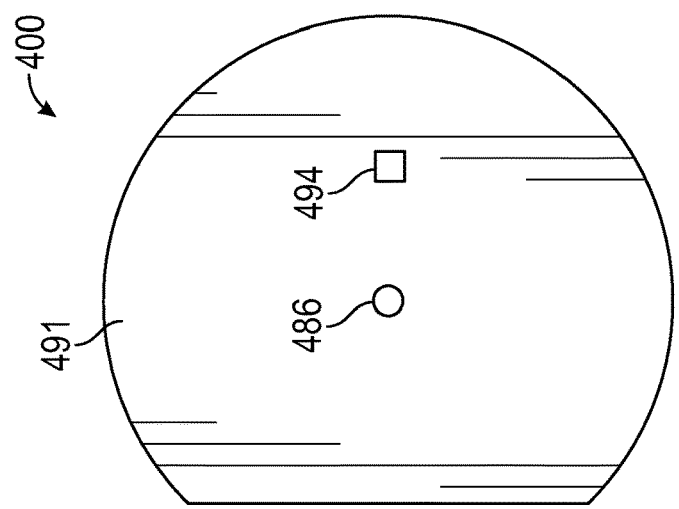
FIGS. 4A-C show the light connector in side, front and back view according to one or more embodiments of the testing apparatus 100.
Figure 4B:
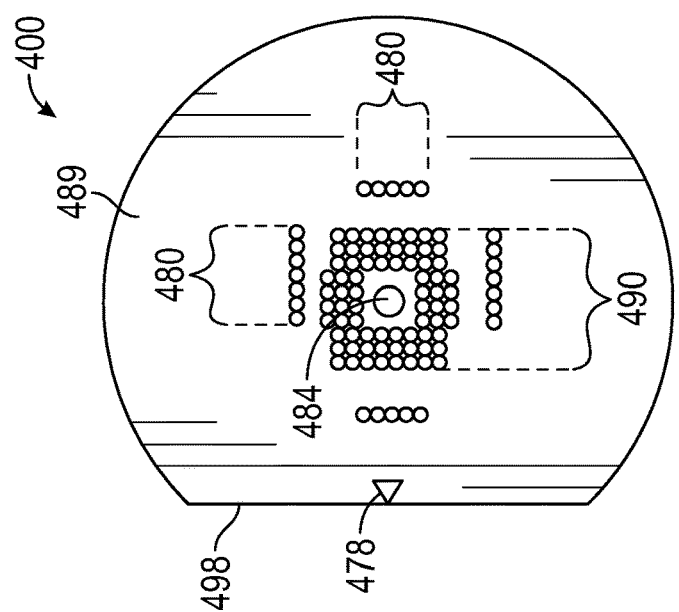
Figure 4A:
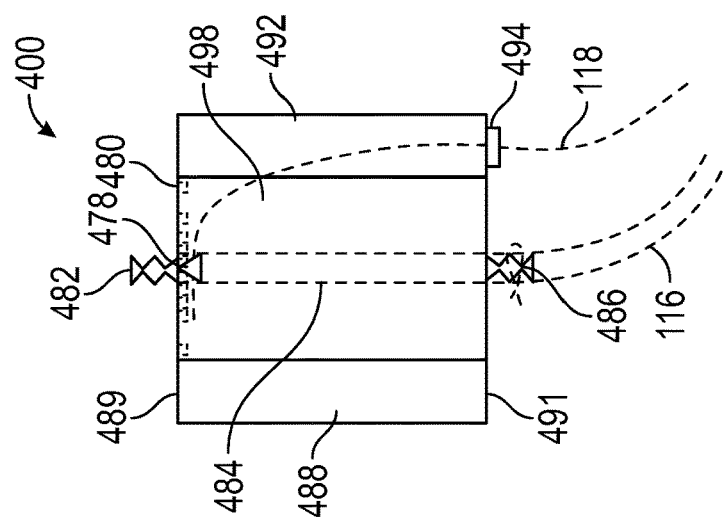

FIGS. 4A-C show optional the light connector (LC) in side, front, and back views according to one or more embodiments of the testing apparatus 100. LC 400 as shown has flat LC front surface 489 and a LC back surface 491. The LC housing 488 between the LC front surface 489 and LC back surface 491 has a generally cylindrical shape except for a portion that is a flat edge 498 on one side that makes the shape asymmetrical. Other configurations of LC housing 488, including symmetrical versions, are envisioned.

As shown in FIG. 4A, LC fluid front connector 482 is positioned on LC front surface 489. LC front fluid connector 482 acts as an extension of the LC fluid conduit 484 and assists in conveying treatment fluid from the light connector 400 into the base housing 300. One of ordinary skill in the art may appreciate that LC front fluid connector 482 may take the form of any common connector for securing a fluid conduit to LC 400, including such connectors as may be required for conveying a treatment fluid at a pressure greater than atmospheric pressure. As well, LC fluid front connector 482 may be configured to frictionally couple with at least a portion of the interior of the primary fluid distribution hole 370.

As shown in FIGS. 4A and C and as previously described, both LC fluid back connector 486 and LC power connector 494 are shown optionally positioned on LC back surface 491. LC fluid back connector 486 in FIG. 4A is shown coupled to primary fluid conduit 116 (in relief). LC fluid back connector 486 may provide not only an external connection to a conduit providing a source of treatment fluid, such as a reactive fluid, such as an acidic fluid, but also, may act as an extension of LC fluid conduit 484, which traverses LC housing 488 from LC back surface 491 to LC front surface 489. LC fluid back connector 486 and primary fluid conduit 116 may both be configured such that they fasten to one another using known and common coupling techniques, such as a clamp, ¼ turn connector or wire tie, to form a fluid-tight seal between the two. A "fluid-tight seal" is such that no interior or exterior sealants, adhesives, or gaskets are required to prevent a loss of fluid containment from between a first surface and a second surface. One of ordinary skill in the art may appreciate that LC fluid back connector 486 may take the form of any common connector for securing a fluid conduit to LC 400, including such connectors as may be required for conveying a treatment fluid at a pressure greater than atmospheric pressure.

Another connector optionally positioned on LC back surface 491 is LC power connector 494. LC power connector 494 in FIG. 4A is shown coupled to power conduit 118 (in relief). LC power connector 494 provides not only an external connection to conduit providing a source of power, but also, connects to power wiring 492 within LC housing 488, which is connected to LC lights 490 positioned just beneath the LC front surface 489. In embodiments, one of ordinary skill in the art may appreciate that LC power connector 494 may take the form of any common connector for securing an electrical conduit to LC 400. LC power connector 494 and power wiring 492 may both be configured such that they fasten to one another using known and common coupling techniques to complete an electrical connection between the two. One of ordinary skill in the art may appreciate that LC power connector 494 may take the form of any common connector for securing an electrical connection to LC 400, including such connectors as may be required for conveying power to generate light through LC lights 490.

FIGS. 4A-C also show that LC alignment mark 478 may be positioned on both LC front surface 489 (FIG. 4B) and flat edge (FIG. 4A). The second base alignment mark 378 is associated with the LC alignment mark 478. The association of second base alignment mark 378 with LC alignment mark 478 is such that the configuration of certain other elements of base housing 300 and light connector 400 are aligned when light connector 400 couples to base housing 300. For example, second base alignment mark 378 and LC alignment mark 478 may be configured such that when the two alignment marks 378, 478 are aligned, LC fluid conduit 484 of light connector 400 is aligned with primary fluid distribution hole 370 of base housing 300 for introducing a treatment fluid into sample recess 360. As another example, when the two alignment marks 378, 478 are aligned, LC lights 490 are aligned with light distribution holes 372 such that light may be transmitted into sample recess 360.

In some embodiments, LC lights 490 may include fiber optics within the interior of and on the outer surface of LC housing 488. In some other embodiments, LC lights 490 may include thin organic light emitting diode (OLED) or light emitting diode (LED) panels for optionally transmitting visible light into sample recess 360. In some alternative embodiments, LC lights may transmit other electromagnetic (EM) frequencies into sample recess 360 through light distribution holes 372 that may assist with the imaging of the core sample in sample recess 360, for example, infrared (IR) light or X-rays.

Second base alignment mark 378 and LC alignment mark 478 may be configured such that when the two alignment marks 378, 478 are aligned, base housing magnetic coupling 380 is aligned with LC magnetic coupling 480 such that a magnetically induced connection forms. LC magnetic coupling 480 is formed of materials subject to magnetism, a magnetic material, or combinations thereof, as previously described. As shown in FIG. 4B for embodiment of the testing apparatus 100, LC magnetic coupling 480 may be configured in an asymmetric pattern, such as previously described for base housing 300. As well, the LC magnetic coupling 480 may be configured in a regular or irregular distribution of its member elements, as previously described for base housing 300. As shown in the embodiment, LC magnetic coupling 480 and base housing magnetic coupling 380 are configured to be asymmetrically coordinated of one another not only in pattern, but also, in coupling mechanism such that the LC magnetic coupling 480 and housing magnetic coupling 380 affirmably interact when positioned together. As seen in FIG. 3D, for example, base housing magnetic coupling 380 may be configured such that the rows of 5 elements may be comprised of magnets and the rows of 7 elements may be comprised of material subject to magnetism. As its reciprocal, LC magnetic coupling 480 may be configured such that rows of 5 elements may be comprised of material subject to magnetism and the rows of 7 elements may be comprised of magnets. Variations in such symmetrical or asymmetrical coordinated configurations, including using configurations of magnets with the same and opposing polarities to attract and repel the LC magnetic coupling 480 to and from the base housing magnetic coupling 380, are envisioned.

Figure 5:
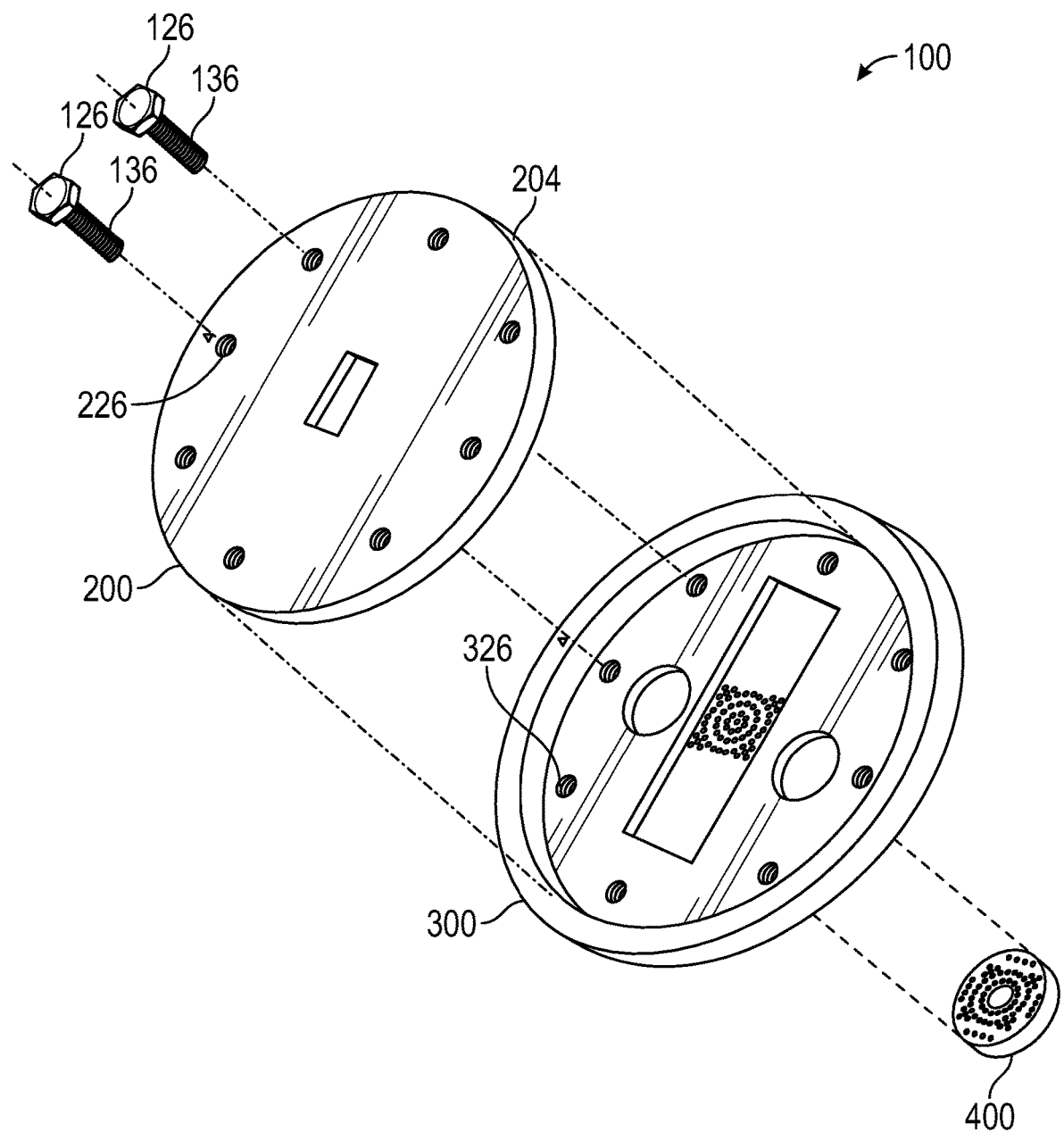
FIG. 5 shows an exploded perspective view of the embodiment testing apparatus 100.

FIG. 5 shows an exploded perspective view of the embodiment testing apparatus 100. According to one or more embodiments, the testing apparatus 100 may be used for observing the interaction and performance of a treatment fluid, such as a reactive fluid, such as an acidic fluid, on a core sample as part of a core sample assembly. The exploded view of the testing apparatus 100 shows the top housing 200, the base housing 300, and the optional light connector 400 relative to one another and how the three components couple to form testing apparatus 100.

Preparing embodiment testing apparatuses like testing apparatus 100 for use encompasses a few steps. A core sample assembly, which includes a core sample to be tested, configured for use in the embodiment testing apparatus is provided. The core sample assembly is introduced into the sample recess such that a core sample is directly observable through the sample viewing window. A core sample assembly (not shown) is introduced into sample recess 360 of base housing 300. Configurations of the core sample assembly may vary depending on the configuration of embodiment testing apparatuses, such as testing apparatus 100, and the dimensions of the sample recess 360; however, it is assumed that the core sample assembly is configured to be positioned entirely within sample recess 360. Three examples of possible core sample assembly configurations are provided in FIGS. 6A-C, as will be described. The core sample is directly fluidly accessible through the primary fluid distribution hole.

Top housing is coupled to the front side of the base housing. Fasteners and other such coupling means for securing one item to another are well understood in the art. Bolts and nuts, screws, tie-wires, and magnetic couplings are examples and are included. Other common means are clearly envisioned. Sealants, adhesives, and gaskets may or may not be used. The top housing 200 is introduced into the top housing recess 340 such that the top housing alignment mark 224 and the first base housing alignment mark 324 are aligned. This ensures that the fastener holes 226, 326 are aligned. The fasteners 126 are introduced into the fastener holes 226, 326 via threads 136 and locked with fastener locks (not shown), which secures top housing 200 to base housing 300. Core sample assembly (not shown) containing the core sample (not shown) is rendered secure and immobile in the sample recess 360 while the top housing 200 is coupled to the base housing 300.

Embodiments of the testing apparatus are configured to secure the core sample assembly without crushing or breaking any part of the core sample assembly—the core sample or the surfaces—when the embodiment testing apparatus is closed. Surface-surface contact fluid-tight seals between the embodiment testing apparatus and the core sample assembly will be describe in the discussion of FIGS. 6A-C.

Optionally, light connector is coupled to the backside of the base housing. To continue the assembly of embodiment testing apparatus 100, light connector 400 may be coupled with base housing 300 such that light connector alignment mark 478 and the second base housing alignment mark 378 are aligned. This ensures that several elements of base housing 300 and LC 400 are aligned and operable. The base housing magnetic coupling 380 is aligned with LC magnetic coupling 480, which permits a magnetic coupling to form between LC 400 and base housing 300. Primary fluid distribution hole 370 on the apparatus back surface 106 is aligned with LC fluid conduit 484 so as to form a continuous fluid flow pathway configured to selectively convey treatment fluid, such as a reactive fluid, such as an acidic fluid, from an external source (via primary fluid conduit 116) into sample recess 360. Light distribution holes 372 on the apparatus back surface 106 are aligned with LC lights 490 to form a continuous pathway configured to convey electromagnetic energy, such as visible light, into sample recess 360. Fasteners and other such coupling means for securing one item to another are well understood in the art and have been previously described.

Optionally, secondary fluid conduit 122 is coupled to the testing apparatus 100 along the apparatus back surface 106. This aligns secondary fluid conduit 122 with the secondary fluid distribution hole 374 and permits fluid accessibility from sample recess 360 for passing of effluent fluid or slurry from testing.

Embodiments of the testing apparatus and its components may be configured to be corrosion-resistant to resist damage from introduced treatment fluids, such as reactive fluids, such as acidic fluids. The top and base housings as well as the optional light connector exterior or body of the testing apparatus may be comprised of materials that are resistant to the treatment fluids, such as reactive fluids, such as acid fluids. Example useful materials may include fluoropolymers and metals like Inconel® 718, Hastelloy®, and Monel®. In some instances, certain parts of top and base housing, such as those surfaces exposed to the treatment fluids, may be clad with such materials resistant to the treatment fluids, whereas other parts of the embodiment testing apparatus may be made of more simple or base materials.

The configuration of the embodiment testing apparatus may permit testing under simulated downhole environmental conditions. In some embodiments, the testing apparatus is configured to withstand testing at conditions understood in the industry to be at high-pressure/high-temperature (HPHT) wellbore conditions. In some embodiments, the embodiment testing apparatus is operable at a temperature between about 20° C. to about 150° C. In some embodiments, the embodiment testing apparatus is operable at an internal pressure in a range of from about atmospheric to about 4000 psi (pounds per square inch).

Core Sample Assembly

Figure 6A:
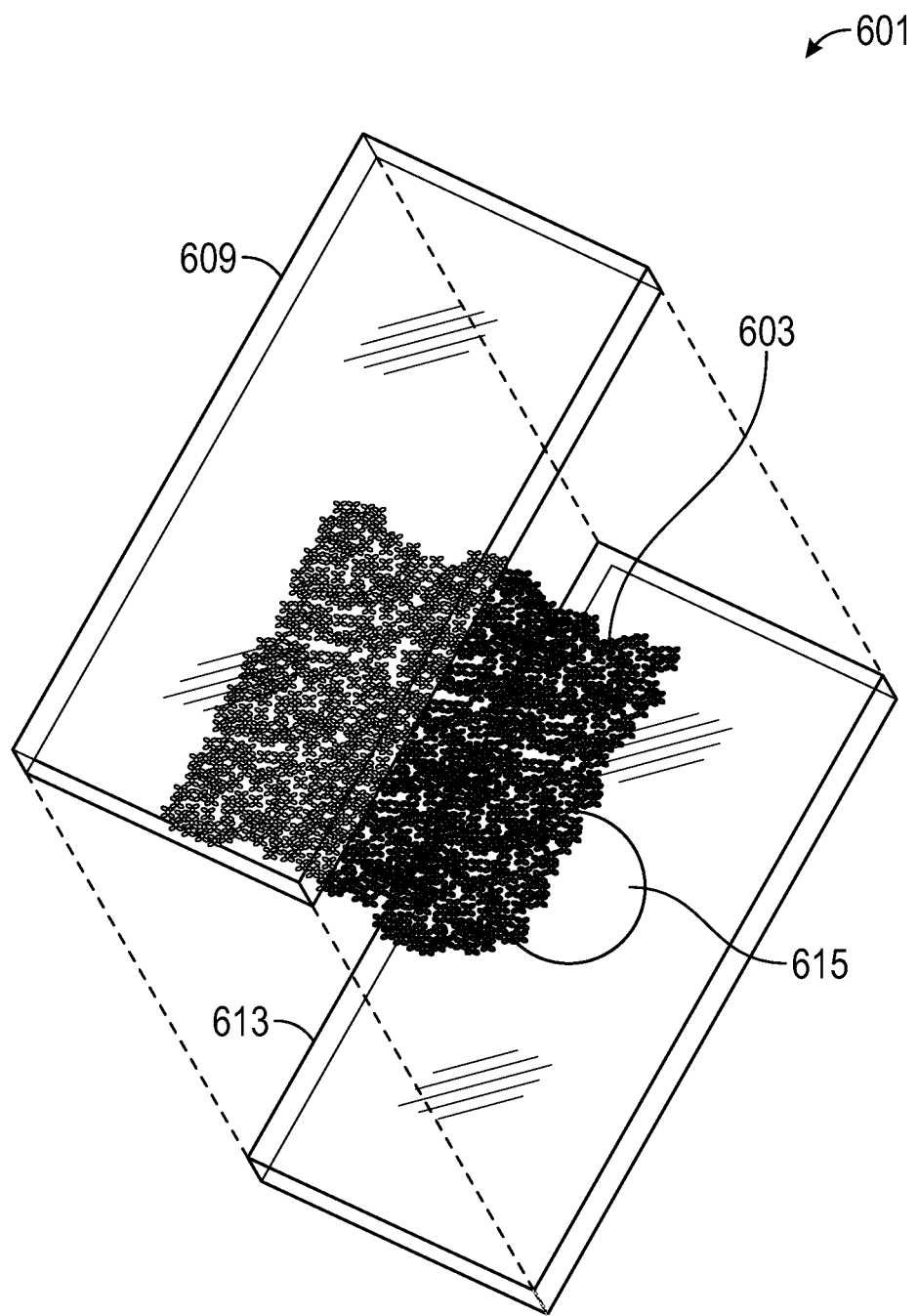
FIG. 6A shows an exploded perspective view of an example of a core sample assembly.
Figures 1, 6B:
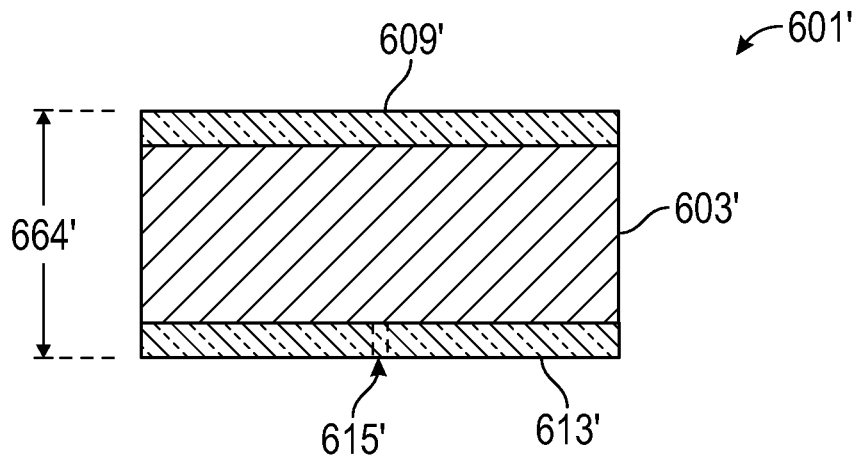
FIGS. 6B-1-3 shows a side view of a second example core sample assembly, and the upper surface and the lower surface of said core sample assembly.
Figures 2, 6B:
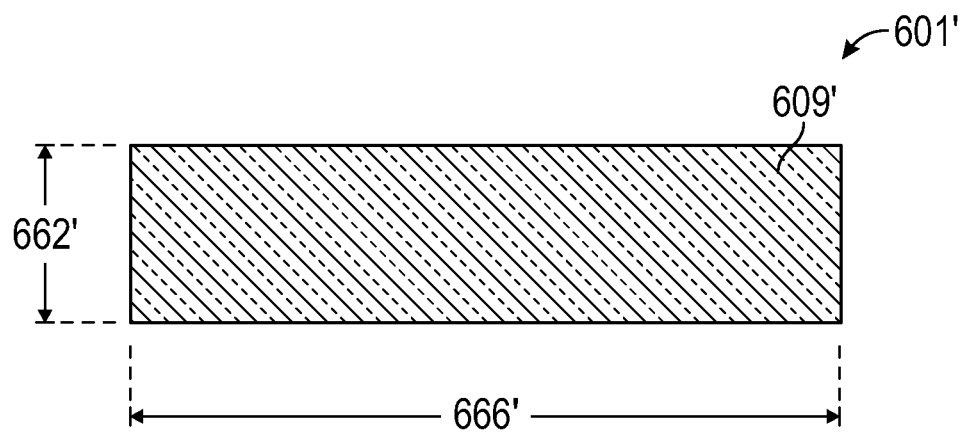
Figures 3, 6B:
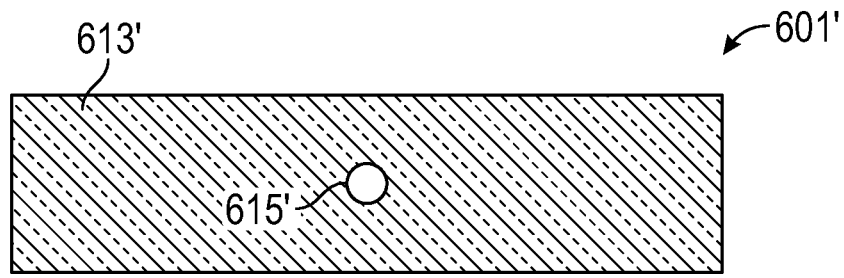
Figures 1, 6C:
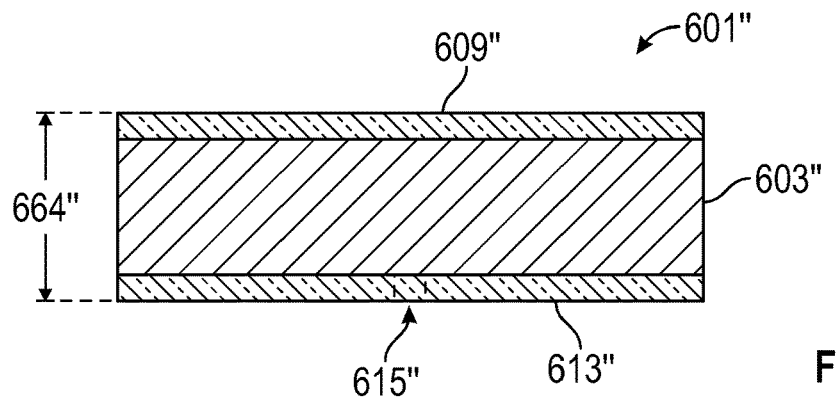
Figures 2, 6C:
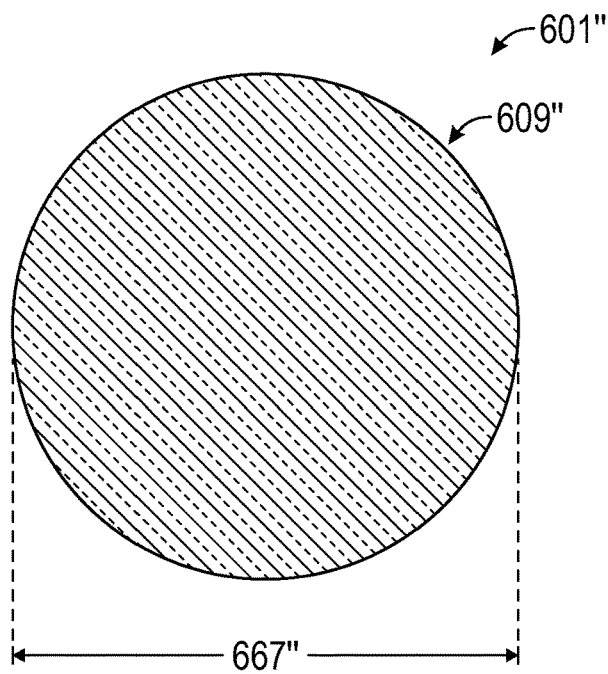
Figures 3, 6C:
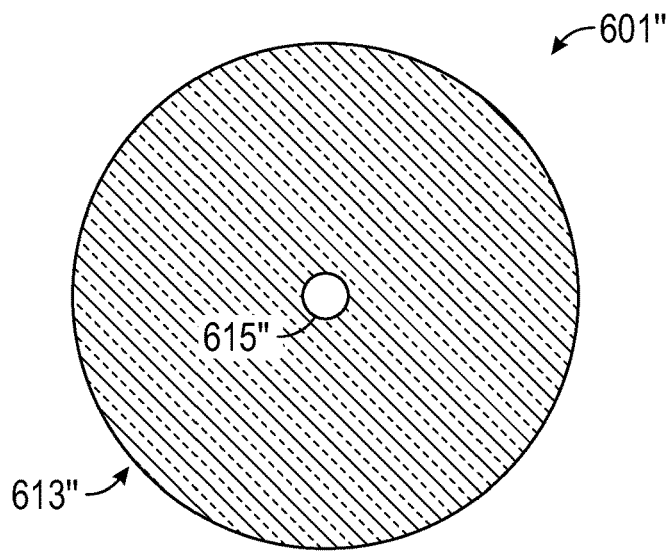

FIG. 6A shows an exploded perspective view of an example of a core sample assembly. FIGS. 6B-1-3 shows a side view of a second example core sample assembly, and the upper surface and the lower surface of said core sample assembly. FIGS. 6C-1-3 shows a side view of a second example core sample assembly, and the upper surface and the lower surface of said core sample assembly. Core sample assemblies 601, 601', and 601" include a core sample 603, 603', and 603", respectively.

Embodiment testing apparatus 100 may be used with a core sample assembly, such as 601 and 601', which is configured for and introduced into the sample recess before an embodiment testing apparatus, such as the testing apparatus 100 of FIG. 1, is fully assembled, as seen in FIGS. 3A-C. FIG. 6A shows an exploded perspective view of an example of a core sample assembly configured for use with an embodiment testing apparatus.

An example of a core sample, (e.g., a core sample 603) as shown in FIG. 6A is formed as a square with a thickness (that is, a square prism) much smaller than its other dimensions. The core sample for use in a core sample assembly may be obtained by cutting a rock sample to form a core slice or coring. Core samples may comprise samples of reservoir and reservoir-like material, such as carbonates, sandstones, or shales, and other materials, and combinations thereof. "Other materials" may include special geological configurations, such as outcrops, intrusions and salt domes, and other specialty testing formats, such as synthetic core samples (that is, non-natural or mathematically designed models on polymers or metal). In some embodiments, the core sample comes from reservoir, which is a hydrocarbon-bearing formation, material. Testing may permit observation and memorialization of the core sample material with different treatment fluids, including reactive fluids, including fluids useful in acidizing operations.

Other configurations of the core sample 603 are envisioned. Core sample 603 may be configured in any regular geometric or non-geometric shape (2D with a thickness or 3D) that meets the bounds of an enclosed sample recess, including a circular shape, a rectangular shape, a triangular shape, or any regular polygon shape, or an irregular shape, to form various prisms. A circular shape (more likely a flat-cylinder or coin-like configuration as the sample has a determinable thickness) may be useful for testing across an entire diameter of a coring from a formation or reservoir. In some embodiments, the core sample may be a slice from a coring and, as such, takes the form of a flat, coin-like cylinder that may have a diameter that up to several inches and a thickness of only a few millimeters. The length and width (or diameter) of the core sample assembly 601 cannot exceed the dimensions of the core sample recess and therefore is limited only by such configuration of embodiment testing apparatuses.

The slice of core sample 603 may be of various thicknesses—from greater than a micrometer to about 15 millimeters (mm). For core sample 603, the back and the front surfaces may be parallel to each other. Both the surfaces may be flat and smooth. A smooth surface may be achieved using specialized cutting and grinding equipment known to those of skill in the art.

In instances where the core sample is less than 2 mm thick, backlighting from the light connector while the core sample is positioned in the core recess may be sufficient to make the opaque sample appear semi-translucent. Under such conditions, direct observation of the treatment fluid, such as a reactive fluid, such as an acidic fluid, interacting with the core sample matrix through the sample viewing window may be feasible.

In FIG. 6A, the core sample 603 is shown positioned within the core sample assembly 601 between two surfaces: upper surface 609 and lower surface 613. In some instances, the entire upper surface 609 is optically transparent; in other instances, for example, a portion of the upper surface positioned above the core sample 603 position is optically transparent. Upper surface may be comprised of any composition where optical transparence occurs over the core sample 603 and that is resistant to compromise by the treatment fluid introduced. Optical transparency permits light transmitted from the light connector passing through light distribution holes and illuminating core sample 603 to traverse out of the testing apparatus through sample viewing window to the observer or the means for memorization.

In some instances, all of the lower surface 613 is optically transparent; in other instances, the portion of the lower surface positioned below the core sample 603 position is optically transparent. Lower surface may be comprised of any composition where optical transparence occurs beneath the core sample 603 and that is resistant to the treatment fluid introduced. Optical transparency permits light to traverse into the core sample 603 to permit observation from the sample viewing window while the core sample assembly 601 is positioned in the sample recess.

The lower surface 613 defines a void 615. The void 615 in lower surface 613 is used in some instances to permit treatment fluid, such as a reactive fluid, such as an acidic fluid, to be introduced into the core sample 603 from primary fluid distribution hole. Void 615 is positioned associated with the primary fluid distribution relative to the sample recess. Such coordination helps to prevent fluid bypass around core sample 603 by creating seals between the core sample apparatus lower surface 613 and the base housing.

For example, as eluded to in FIG. 6A, the upper surface may be a flat, rectangular slide made of glass or polymer, and of similar size to those used in microscopes. The lower surface may be configured of a similar material (glass or polymer) and have a similar size as the upper slide, but the lower surface includes a void to permit treatment fluid to be introduced into the core sample at the designated positions within the sample recess of the embodiment treatment apparatus.

In some instances, the upper surface is rigid and unyielding. In some instances, the lower surface is rigid and unyielding. Glass and some polymers, like polycarbonates, may be examples of a rigid material that is also transparent, that is chemically resistant to the treatment fluid, and can withstand a pressure differential between its two sides. In some other instances, the upper surface is resilient and yielding, that is, the material yields to a force applied and then rebounds or reforms its original shape when the force is removed. In some instances, the lower surface is resilient and yielding. Silicone rubbers, some polyurethanes, and some partially cured epoxy resins, may be examples of resilient materials operable to withstand operational conditions while also providing adequate transparency. In some instances, both rigid and resilient types of materials may be used in a core sample assembly. For example, a rigid surface may be used against the surface of the core sample to provide a fluid seal to prevent fluid bypass, and a resilient surface may be used to couple with the top housing proximate to the viewing window. Both the rigid surface and the resilient surface may be bonded to one another using means known to one of skill in the art.

Thickness of the upper and lower surfaces may be based upon the pressure requirement for the testing of the core sample. For example, the thickness of the upper or lower surface, or both, may be up to several millimeters thick. If fluid flow is introduced into the testing apparatus at a pressure similar to the downhole environment, the upper surface may have to maintain a differential pressure between the downhole environment and external conditions during introduction and use of the treatment fluid as the viewing window is present. In such an instance, the upper surface would be much thicker than a similar surface that is merely preventing slightly greater than surface pressures from escaping. Similar adjustments may be made to the lower surface to accommodate for the introduction and passing of pressurized fluids while also permitting light to enter the sample recess.

The top surface of the core sample 603 may be configured such the upper surface 609 mates with the top surface of the core sample 603. The surface of the core sample 603, for instance, may be ground flat and polished to create a glass-like smooth surface configured to mate with a similar smooth surface of upper surface 609. As well, the lower surface of the core sample 603 may be configured such that the bottom surface 613 mates with the bottom surface of the core sample 603 in a similar manner. With both upper and lower surfaces 609, 613 mated, the core sample assembly is formed. When the three elements (603, 609, 613) are assembled into core sample assembly 601, one or more fluid-tight seals are capable of being formed. The fluid-tight seals form, it is believed, when the core sample assembly 601 is in the sample recess when the top and base housings are coupled together during the assembly of the embodiment testing apparatus due to pressure being applied to the core sample assembly. During operation of the embodiment testing apparatus, the fluid tension of the treatment fluid, even under potentially reservoir-like temperatures and pressures, is insufficient to overcome the fine gap between the surface-surface contacts, effectively creating a fluid-tight seals. As well, it is envisioned that a similar surface-surface contact fluid-tight seal forms between the lower surface 613 and the lower surface of the core sample 603 in the locations where the void 615 is not present, which assists in routing treatment fluid to a specific contact location for and into the core sample 603.

In some instances, the core sample assembly 601 may use sealants, adhesives or gaskets to prevent fluid bypass between the upper surface 609 and the core sample 603, between the core sample 603 and the lower surface 613, and between the upper surface 609 and the lower surface 613 where the core sample 603 is not present. Such sealants, adhesives or gaskets are used within the core sample assembly and not on the embodiment testing apparatus. In such instances, the introduced sealant may be transparent, may be acid resistant, and may be chemically inert to the introduced treatment fluids. In some other embodiments, the introduced seal may be configured to withstand elevated temperatures, such as those experienced in a high-pressure/high-temperature (HPHT) environment downhole. Seals used in HPHT-type environments may need to be resistant to the introduced fluids or byproducts of reactions that may occur under such conditions.

FIG. 6B-1-3 shows an end, upper surface and lower surface of a second example of a core sample assembly 601' that may be used with embodiment testing apparatus. An example of a core sample—a core sample 603'—is formed as a rectangular prism with a core sample length 666' and a core sample width 662', which are substantially similar to sample recess length and sample recess width of sample recess of an embodiment testing apparatus. Core sample assembly thickness 664' is at or less than the sample recess depth because core sample assembly 601' includes upper surface 609' and lower surface 613'.

In the second example, it can be envisioned that both upper surface 609' and lower surface 613' are comprised of transparent sealant material that adheres to the core sample 603' surface. The composition of the sealant may be varied depending on a variety of reasons, including type of treatment fluid, testing conditions, and transmissiveness of the surfaces 609', 613'.

FIG. 6B-3 shows the lower surface 613' having voids 615'. Such a configuration may be supportive of a base housing with a primary fluid distribution hole and a side secondary distribution hole.

FIG. 6C-1-3 shows an end, upper surface and lower surface of a third example of a core sample assembly 601" that may be used with embodiment testing apparatus. An example of a core sample—a core sample 603"—is formed as a thick cylinder with a core sample diameter 667". The thickness of the core sample may be several millimeters thick. Testing such a large core sample may require an embodiment testing apparatus that has the ability to expand to accommodate the thickness of the core sample, such as embodiment testing apparatus 1200 (to be detailed). Core sample assembly 601" includes upper surface 609" and lower surface 613".

In this example, upper surface 609" and lower surface 613" are envisioned to be a transparent, rigid, and unyielding material, such as glass or polycarbonate. Such materials are useful when the sample size creates a core sample 603" that is weighty. Rigid upper and lower surfaces 609", 613" provide for ease of handling the sample when the core sample assembly 601" is assembled as well as for disassembly and cleaning after the test is performed, and reuse.

FIG. 6C-3 shows the lower surface 613" having a single, centralized void 615". Such a configuration may be supportive of a base housing with a primary fluid distribution hole in the center of the base housing and one or more secondary fluid distribution holes along the side of instead of through the bottom of the base housing.

Second Embodiment Testing Apparatus

FIGS. 7A-C show an assembled testing apparatus in front, side, and back views according to one or more embodiments 700. The embodiment testing apparatus 700 may have similar use functionality to apparatus 100 in relation to how the core sample assembly 601 (or 601') may be introduced and a treatment fluid used on it with the testing apparatus. However, there are several structural differences to testing apparatus 700 that are of note and will be described in detail.

Testing apparatus 700 has an apparatus front surface 702, an apparatus side edge 704 and an apparatus back surface 706. Embodiments of the apparatus 700 include several exterior-observable components that are coupled, including yoke 800, base housing 900, and top housing 1000. Optional light connector 400', which is also present, has been effectively described previously as light connector 400.

Testing apparatus 700 has an apparatus diameter 708 and an apparatus thickness 710 as seen in FIG. 7B.

Several features are readily apparent from the view of testing apparatus 700 in FIGS. 7A-C that are common with testing apparatus 100 but with slight configuration variations. Given that the functionally is equivalent, the introduction of each will be brief. Sample viewing window 220' in FIG. 7A is configured slightly different to show more of the core sample assembly. The configuration of optional light connector 400' is slightly different in that the LC housing 488' is fully cylindrical. As well, LC back surface 491' has a LC alignment mark 478. Everything else is as previously described.

FIG. 7B shows that top housing 1000 has a ribbed edge 1005 that extends the apparatus diameter 708 to a diameter greater than base housing 900, as can be seen from the back view of FIG. 7C. The ribbed edge 1005 configuration provides a grip that permits the top housing 1000 to more easily rotate using a frictional grip on the external contacting surface and applying torque to top housing 1000.

FIGS. 8A-C show the yoke 800 in front, side, and back views according to one or more embodiments of the testing apparatus 700. Yoke 800 may be described as having a "tiered cake" or "stair step" configuration. The yoke 800 has two sections: a top yoke section 813 and a bottom yoke section 814. The yoke 800 has two yoke front-facing surfaces: 802a (top yoke front surface) and 802b (bottom yoke front surface). Yoke 800 also has two side-facing edges: 804a (top yoke side edge) and 804b (bottom yoke side edge). Yoke 800 has a yoke back surface 806. Of the surfaces of yoke, only top yoke front surface 802a is visible externally as a portion of apparatus front surface 702.

Configurations of yoke 800 have a paneless sample viewing window 220'.

Yoke 800 is also shown to have a top yoke section diameter 809 and a bottom yoke section diameter 808, which is greater than top yoke section diameter 809. Bottom yoke section diameter 808 is effectively the yoke diameter. Both diameters 808, 809 are less than apparatus diameter 708. Yoke 800 also has two yoke thicknesses: a top yoke section thickness 812 and a bottom yoke section thickness 811. Additively, the two yoke thicknesses 811, 812 add up to the yoke thickness 810. Yoke thickness 810 is less than the apparatus thickness 710.

The yoke 800 does not have any internal or external threads along either top yoke side edge 804a or bottom yoke side edge 804b.

FIG. 8A shows yoke alignment mark 824 on bottom yoke front surface 802b. Yoke alignment mark 824 is similar in configuration and function as previously described alignment marks.

In some embodiments, the yoke 800 includes yoke stops 817 that extend a fixed length from the yoke back surface 802. In some other embodiments, the yoke 800 includes yoke stop gaps 815 that extend a fixed depth into the bottom yoke section 814 of the yoke 800. In some other instances, such as shown in FIGS. 8B-C, both yoke stops 817 and yoke stop gaps 815 are present.

FIGS. 9A-C show the base housing 900 in top, side, and back views according to one or more embodiments of the testing apparatus 700. Base housing 900 has a base housing side edge 904 and a base housing back surface 906. Base housing side edge 904 comprises a portion of apparatus side edge 704. Base housing back surface 906 comprises apparatus back surface 706. Base housing 900 has several front-facing surfaces. The front edge 352 of base lip 350, top housing and yoke recess front surface 348', and sample recess front surface 361 all combine to provide the front-facing surfaces of base housing 900; however, none are visible from the front view when testing apparatus 700 is fully assembled.

Base housing 900 along its exterior surface has a base housing thickness 910 and a base housing diameter 908. Top housing and yoke recess 340' has a top housing and yoke recess diameter 942. Top housing and yoke recess diameter 942 is greater than bottom yoke section diameter 808.

Base housing 900 has a configuration similar to base housing 300, but with slight variations. Top housing and yoke recess 340' has many similar configurational aspects as top housing recess 340. In FIG. 9C, base housing magnetic coupling 380' is in a dual bar-like configuration; however, functionally for coupling LC 400', it is similar to the prior-described base housing magnetic coupling 380.

The testing apparatus is configured with a sample recess 360'.

Testing apparatus is configured with a primary fluid distribution hole 370 and light distribution holes 372.

FIGS. 9A and B show that along top housing recess edge 346 of base lip 350 there is internal threading 946.

In some embodiments, the base housing 900 includes base housing stops 915 that extend a fixed length from the top housing and yoke recess front surface 348'. In some other embodiments, the base housing 900 includes base housing stop gaps 917 that extend a fixed depth into the top housing and yoke recess front surface 348' of the base housing 900. In some other instances, such as shown in FIG. 9A, both base housing stops 915 and base housing stop gaps 917 are present.

Yoke stop gaps 815 and base housing stops 915 are configured and coordinated. For example, when yoke 800 is positioned within top housing and yoke recess 340', base housing stops 915 will fit within yoke stop gaps 815 such that yoke 800 can no longer rotate against base housing 900. Yoke stops 817 and base housing stop gaps 917 are similarly yet oppositely configured to the same purpose. The configuration of stops and stop gaps between the yoke and the base housing can allow other features, for example, the sample viewing window 220, to be properly aligned for the assembly of the embodiment testing apparatus.

Although not shown in FIGS. 9A-C, in some embodiments of the base housing there are secondary fluid distribution holes for withdrawing treatment fluid residual, introducing treatment fluid or components of treatment fluids, or both, similar to as having been described previously.

FIGS. 10A-C show the top housing 1000 in front, side, and back views according to one or more embodiments of the testing apparatus 700. Top housing 1000 has a top housing front surface 1002, a top housing side edge 1004, and several back-facing surfaces. Top housing front surface 1002 comprises part of apparatus front surface 702. Ribbed edge 1005 comprises part of apparatus side edge 704. Back-facing edges of top housing 1000 include top housing back edge 1006a, top housing backfacing yoke edge 1006b and top housing backfacing base lip edge 1006c. Inside-facing edges of top housing 1000 include top housing yoke top edge 1007a and top housing yoke bottom edge 1007b.

Top housing 1000 is also shown to have a top housing thickness 1010 and a top housing diameter 1008. For testing apparatus 700, top housing thickness 1010 is less than apparatus thickness 710. Top housing diameter 1008 is equal to the apparatus diameter 708.

There are other diameters of note in describing top housing 1000. FIGS. 10B and C show the top housing threading diameter 1023 associated with external threading 1046. Top housing threading diameter 1023 corresponds to the diameter of top housing and yoke recess diameter 942 of base housing 900 such that the top housing 1000 and the base housing 900 may threadily couple when assembling testing apparatus 700.

There are also other thicknesses that help describe top housing 1000. Top housing thickness 1010 describes the total thickness of top housing 1000; however, this can be divided amongst several portions of meaning. The thickness of top housing 1000 associated with the ribbed edge 1005 is measurable as ribbed edge thickness 1033. The remainder of the top housing thickness 1010 is associated with external threading 1046, and external threading thickness 1031.

A yoke recess 1040 is formed within the body of top housing 1000 configured to accept yoke 800 into top housing 1000. Yoke 800 fits within yoke recess 1040 such that the top yoke front surface 802a and top housing front surface 1002 sit flush with each other when testing apparatus 700 is assembled; however, it can be envisioned that other variations are feasible. As well, yoke back surface 806 and top housing back edge 1006a also sit flush with each other when assembled, although it can be envisioned that other variations may be feasible.

Several dimensions of the yoke 800 and the top housing 1000 are configured to reciprocate with one another. Top housing yoke bottom diameter 1021 corresponds to the diameter of the bottom yoke section diameter 808 of the yoke 800 such that the bottom yoke section 814 may fit within the lower portion of yoke recess 1029. Top housing yoke top diameter 1009 corresponds to the diameter of the top yoke section diameter 809 such that the top yoke section 813 may fit within the upper portion of yoke recess 1027 and be observed as part of the exterior of testing apparatus 700 when coupled with top housing 1000. The bottom yoke thickness 1011 is similar to the bottom yoke section thickness 811 such that in embodiment testing apparatus 700 entire bottom yoke section 814 fits within lower portion of yoke recess 1029. The top yoke thickness 1012 is similar to the top yoke section thickness 812 such that in embodiment testing apparatus 700 the entire top yoke section 813 fits within upper portion of yoke recess 1027. Top yoke side edge 804a fits within top housing yoke top edge 1007a and bottom yoke side edge 804b fits within top housing yoke bottom edge 1007b.

FIGS. 10B and C show that along top housing side edge 1004 there is external threading 1046. The configuration of external threading 1046 corresponds to the internal threading 946 such that the external threading 1046 and the internal threading 946 are operable to couple together. Top housing 1000 and the base housing 900 are joined by threadily coupling the top housing 1000 into the base housing 900 until one of the following occurs first: (1.) the internal and external threads 1046, 946 are played out; (2.) top housing back edge 1006a contacts top housing and yoke recess front surface 348'; or (3.) a pair of stop/stop gap prevent the yoke descending further onto the top housing and yoke recess front surface. The stop/stop gap interaction will be described further. In some embodiments, the external threading thickness 1031 of external threading 1046 of top housing 1000 is equal to or greater than the top housing recess depth 344 of internal threading 946 of base housing 900.

Figure 11:
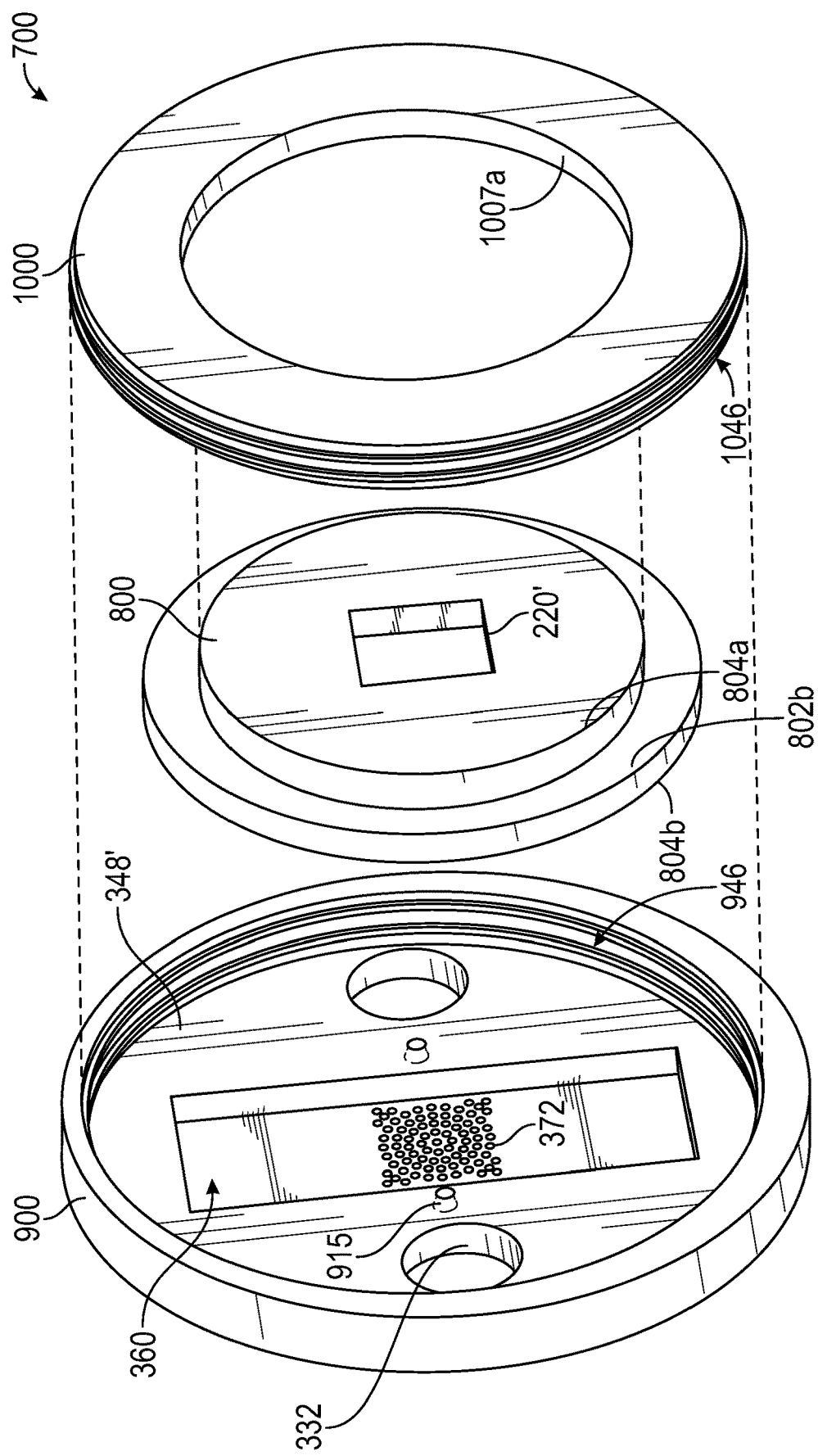
FIG. 11 shows an exploded perspective view of a portion of the embodiment testing apparatus 700.

FIG. 11 shows an exploded perspective view of the embodiment testing apparatus 700. According to one or more embodiments, the testing apparatus 700 may be used for observing the interaction and performance of a treatment fluid on a core sample as part of a core sample assembly. The exploded view of the testing apparatus 700 shows the top housing 1000, the base housing 900, and the yoke 800 relative to one another and how the three components couple to form testing apparatus 100. Light connector 400' is not presently shown; however, its function and coupling with the base housing 900 has been previously described and shown in similar embodiment testing apparatuses.

Preparing embodiment testing apparatus 700 for use encompasses a few steps. The core sample assembly is positioned within the sample recess such that a core sample is directly observable through the sample viewing window. A core sample assembly, such as the configurations previously described, is introduced into sample recess 360 of base housing 900. The core sample assembly is configured to be positioned entirely within sample recess 360. The core sample is directly fluidly accessible through the primary fluid distribution hole. Yoke 800 is introduced into the top housing and yoke recess 340' such that yoke alignment mark 824 and first base housing alignment mark 324 are aligned; base housing stops 915 fit into yoke stop gaps 815, if present; and yoke stops 817 fit into base housing stop gaps 917, if present.

The length of stops 817, 915 and the depth of stop gaps 815, 917 may be used to prevent over-pressuring of the core sample assembly 601 in core sample recess 360 by the yoke 800. As well as preventing over-pressurization and assisting with alignment of the yoke 800 with the base housing 900, the stops 817, 915 and the stop gaps 815, 917 may also prevent the yoke 800 from turning or spinning when the top housing 1000 is threadily fitted to base housing 900.

Continuing the assembly process, top housing couples to the front side of the base housing and is secured in place with a fastening means. The top housing 900 is introduced into the portion of the top housing and yoke recess 340' not occupied by the yoke 800. Coupling occurs by threadily engaging external threading 1046 of top housing 1000 with internal threading 946 of base housing 900 until the rotation of top housing 1000 stops. Yoke 800 occupies yoke recess 1040 of top housing 1000 when base housing 900 couples with top housing 1000.

Optionally, light connector is coupled to the back side of the base housing with a second fastening means. Although not shown in FIG. 11, to continue the assembly of embodiment testing apparatus 700, light connector 400' is coupled with base housing 900 as previously described in other embodiments.

Optionally, one or more secondary fluid conduits 122 may be coupled as previously described. In such embodiments, the testing apparatus 700 has supporting attachments for such connectors.

Third Embodiment Testing Apparatus

Figure 12B:
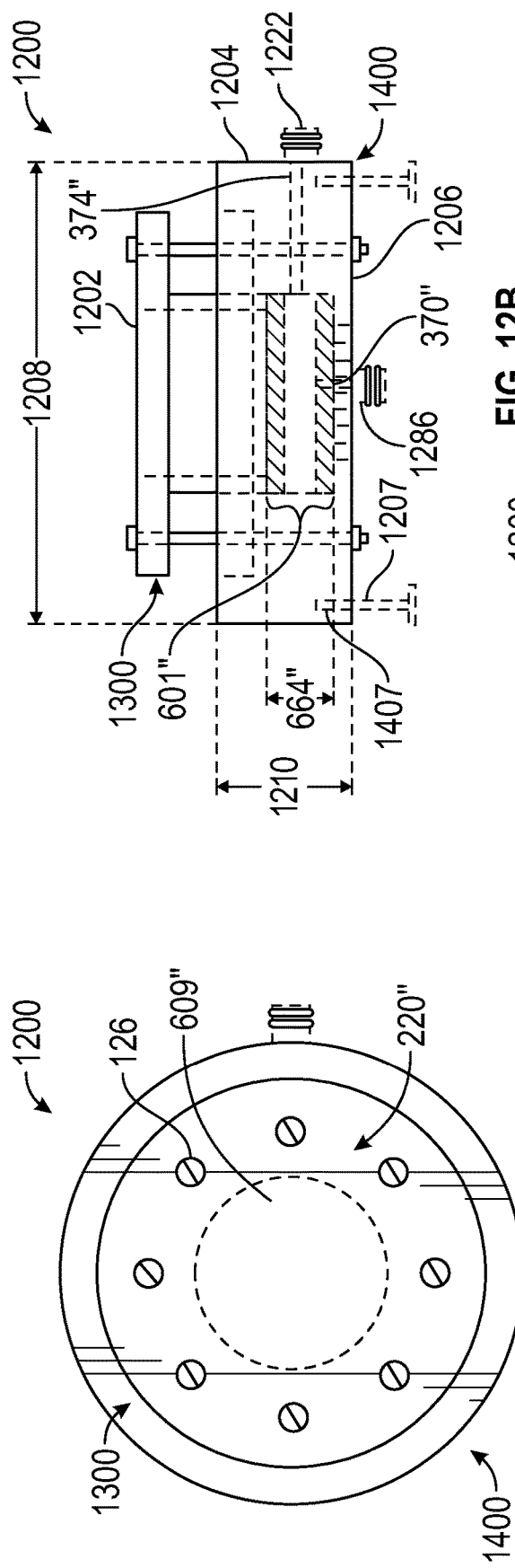
FIGS. 12A-C show an assembled testing apparatus in front, side, and back views according to one or more embodiments.
Figure 12C:
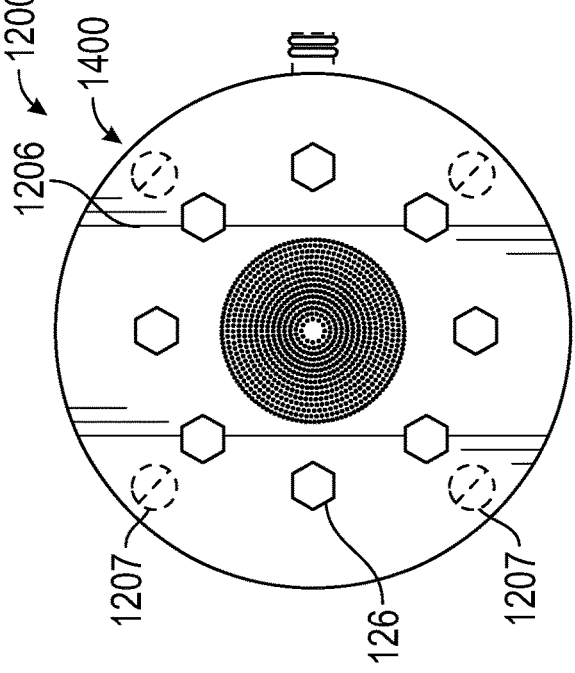
Figure 12A:
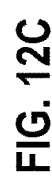

FIGS. 12A-C show an assembled testing apparatus 1200 in front, side, and back views according to one or more embodiments. The testing apparatus 1200 has a similar purpose as testing apparatuses 100 and 700; however, its configuration varies in certain ways from the two embodiment testing apparatuses previously described. The configurational differences can be attributed to the handling of a cylindrical "core slice" as the core sample. Potentially, greater operating pressures and treatment fluid volumes may also be explored. One of skill in the art will note that the vision of embodiment testing apparatus 1200, just as with testing apparatuses 100 and 700, include versions that may be scaled upwards or downwards in size and capacity to accommodate different amounts of treatment fluid, sample sizes, and testing conditions.

Testing apparatus 1200 has an apparatus front surface 1202, an apparatus side edge 1204 and an apparatus back surface 1206. Embodiments of the apparatus 1200 include several exterior-observable components, including top housing 1300 and base housing 1400.

Testing apparatus 1200 has an apparatus diameter 1208 and an apparatus thickness 1210 as seen in FIG. 12B.

Several features previously described can be seen in FIGS. 12A-C. Upper surface 609" (in relief) is visible through sample viewing window 220". Sample viewing window 220" provides a circular view of core sample assembly 601". Core sample assembly 601" is positioned within base housing 1400. The core sample assembly 601" is held in position by downward pressure along the circular outer edge of upper surface 609" applied by coupled top housing 1300. Fasteners 126 couple top housing 1300 to base housing 1400.

Embodiment testing apparatus 1200 does not show optional light connector. Rather, primary fluid distribution hole 370" is coupled to a primary fluid coupling connector 1286 (in relief). Primary fluid coupling connector 1286 may be coupled to a primary fluid conduit, such as primary fluid conduit 116 of FIGS. 1B, as previously described.

Testing apparatus 1200 does show that secondary fluid distribution hole 374" is coupled to secondary fluid coupling connector 1222 (in relief). Secondary fluid coupling connector 1222 may be coupled to a secondary fluid conduit, such as secondary fluid conduit 122 of FIG. 1B, as previously described.

Several testing apparatus stand legs 1207 (in relief) are coupled to the embodiment testing apparatus 1200 through the bottom side. This permits the testing apparatus 1200 to be placed on a work bench while providing appropriate clearance for connectors and tubing coupled to the bottom side. Testing apparatus stand legs 1207 couple with the testing apparatus 1200 via stand holes 1407 defined by base housing 1400. In some instances, stand holes 1407 may be threaded to secure testing apparatus stand legs 1207 in position.

Figure 13B:
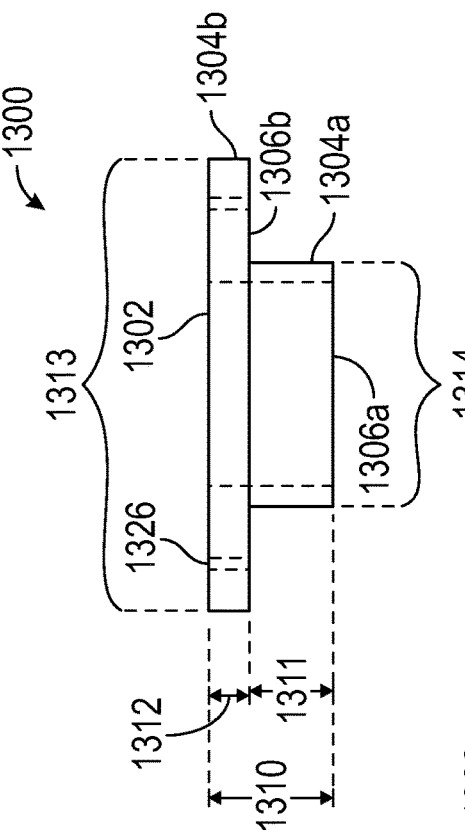
FIGS. 13A-C show the top housing in front, side, and back views according to one or more embodiments of the testing apparatus 1200.
Figure 13C:
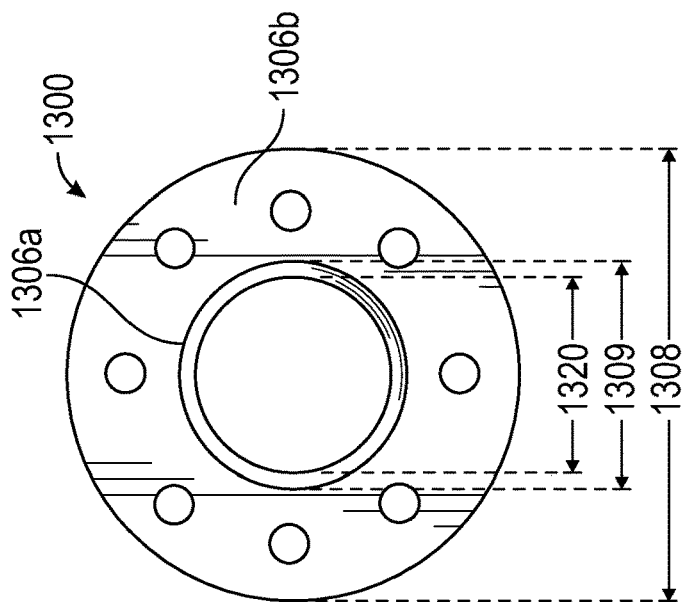
Figure 13A:
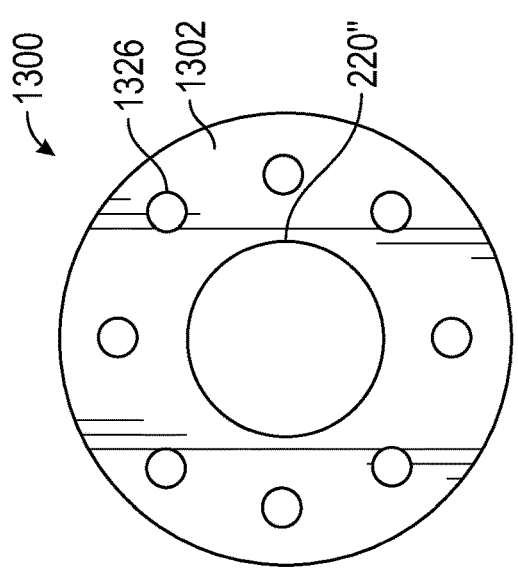

FIGS. 13A-C show the top housing 1300 in front, side, and back according to one or more embodiments of the testing apparatus 1200. Top housing 1300 has a top housing front surface 1302, which is part of the apparatus front surface 1202. Top housing is made of two different sections: a top section 1313 and a bottom section 1314. Each section has its own side edge and back-facing surface. Top section 1313 has top section side edge 1304b and top section back surface 1306b. Bottom section 1314 has bottom section side edge 1304a and bottom section back surface 1306a.

Top housing 1300 has two sets of diameters—one for each section. Top section diameter 1308 is the broadest diameter for the top housing 1300 and is affiliated with top section side edge 1304b. Bottom section diameter 1309 is narrower and is affiliated with bottom section side edge 1304a. There is a third diameter for the paneless sample viewing window 220" that is sample viewing window diameter 1320, which is less than bottom section diameter 1309.

Top housing 1300 has an overall thickness 1310. Top housing 1300 is also shown to have a top section thickness 1312 associated with top section 1313. Bottom section thickness 1311 is associated with bottom section 1314.

Top housing 1300 also has fastener holes 1326. Fastener holes 1326 are configured 1200 to permit a portion of fasteners 126 to pass through the top housing 1300.

Figure 14B:
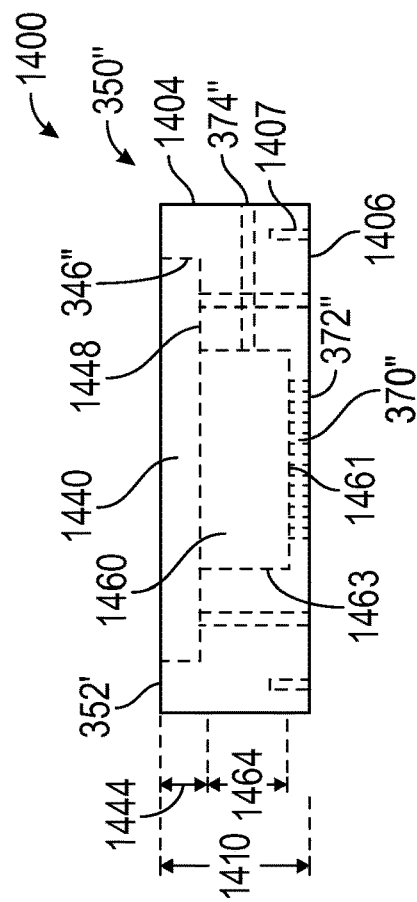
FIGS. 14A-C show the base housing in front, side, and back according to one or more embodiments of the testing apparatus 1200.
Figure 14C:
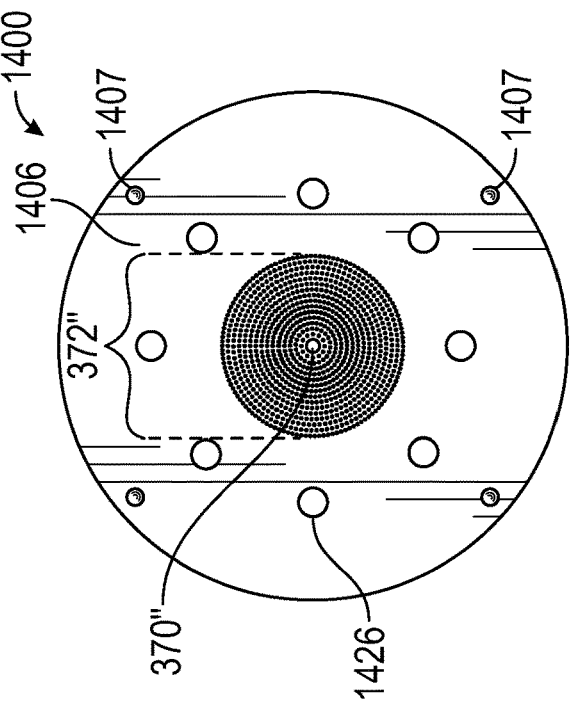
Figure 14A:
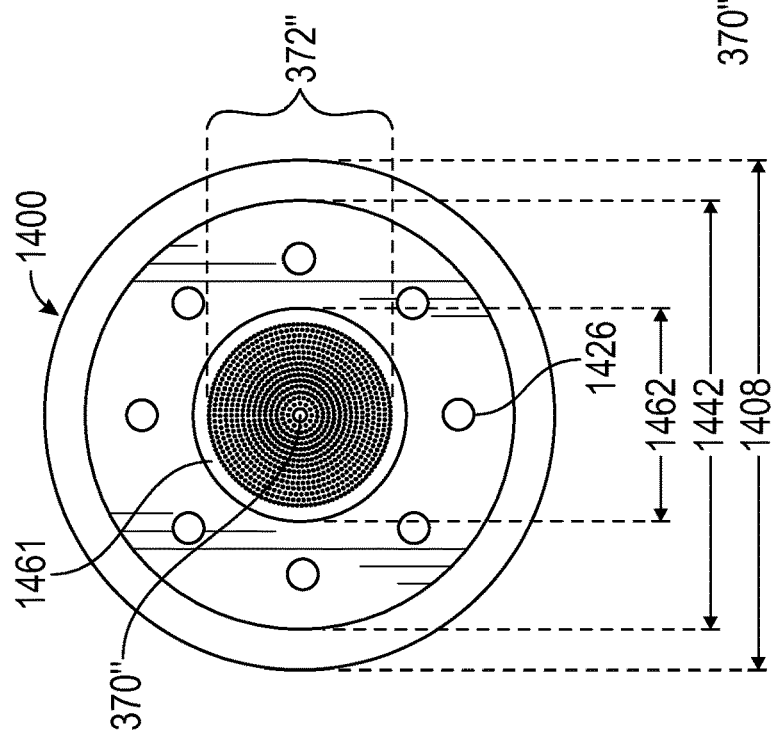

FIGS. 14A-C show the base housing 1400 in front, side, and back according to one or more embodiments of the testing apparatus 1200. Similar to the configuration of embodiment testing apparatus 100, the base housing side edge 1404 and base housing back surface 1406 are the same as apparatus side edge 1204 and an apparatus back surface 1206 of embodiment apparatus 1200. In FIG. 14B, front edge 352' of base lip 350" extends forward and is part of the apparatus front surface 1202. The other front-facing surfaces of embodiment testing apparatus 1200 are sample recess front surface 1461, which is associated with the sample recess 1460, and top housing recess front surface 1448.

Base housing 1400 has several diameters of note. Base housing diameter 1408 is the same as apparatus diameter 1208. Base housing 1400 also has top housing recess diameter 1442 that is less than the base housing diameter 1408. Top housing recess 1440 is configured to receive the top section 1313 of the top housing 1300. Sample recess diameter 1462 is configured such that the bottom section 1314 of the top housing 1300 similarly may fit into the base housing

1400. Core sample assembly 601" have an appropriate diameter configuration to fit into sample recess diameter 1462 when embodiment testing apparatus 1200 is used.

Base housing 1400 also has several thicknesses. Base housing has base housing thickness 1410, which is the same as apparatus thickness 1210. Top housing recess thickness 1444 is associated with the top section thickness 1312 of top section 1313. In some embodiments, when top housing 1300 is introduced into base housing 1400, the top housing recess thickness 1444 and the top section thickness 1312 are configured as such that top housing front surface 1302 sits flush with front edge 352'. In other embodiments, such as shown in FIG. 12B, the surfaces are not flush.

The testing apparatus is configured with a sample recess. Sample recess depth 1464 as determined along sample recess edge 1463 of sample recess 1460 is configured to accommodate bottom section thickness 1311 of bottom section 1314 of top housing 1300. In some embodiments, bottom section thickness 1311 is less than sample recess depth 1464. In such embodiments, the difference between the bottom section thickness 1311 and sample recess depth 1464 is to accommodate the core sample assembly thickness 664" of core sample assembly 601. When introduced into sample recess 1460, as seen in FIG. 12B, core sample assembly 601" resides on sample recess front surface 1461.

Testing apparatus is configured with a primary fluid distribution hole. Base housing 1400 includes primary fluid distribution hole 370" and light distribution holes 372", both of which function in this embodiment testing apparatus 1200 as previously described.

In the embodiment of base housing 1400, the light distribution holes 372" are configured in a circle pattern to maximize backlighting of core sample assembly 601". The light distribution holes in this instance are configured not only to provide space for primary fluid distribution hole 370", but also, to provide for a solid ring along the outer periphery of sample recess front surface 1461. This space approximately mimics the footprint of where the bottom section back surface 1306a of top housing 1300 contacts upper surface 609 of core sample assembly 601". The space provides a visual reminder to ensure that core sample assembly 601" is configured and positioned appropriately for use when top housing 1300 and base housing 1400 are coupled.

Although not shown in FIGS. 14A-C, one or more secondary fluid distribution holes 374" for withdrawing treatment fluid residual similar to as having been described previously.

Base housing 1400 also has fastener holes 1426. Fastener holes 1426 are configured for embodiment testing apparatus 1200 to permit a portion of fasteners 126 to pass through the base housing 1400.

Optionally, testing apparatus 1200 has recesses (stand holes 1407) for permitting apparatus stand legs 1207 to be coupled to the base housing 1400. As previously described, this may permit testing apparatus 1200 to be positioned level and on a flat support surface for allowing the test to be performed.

Figure 15:
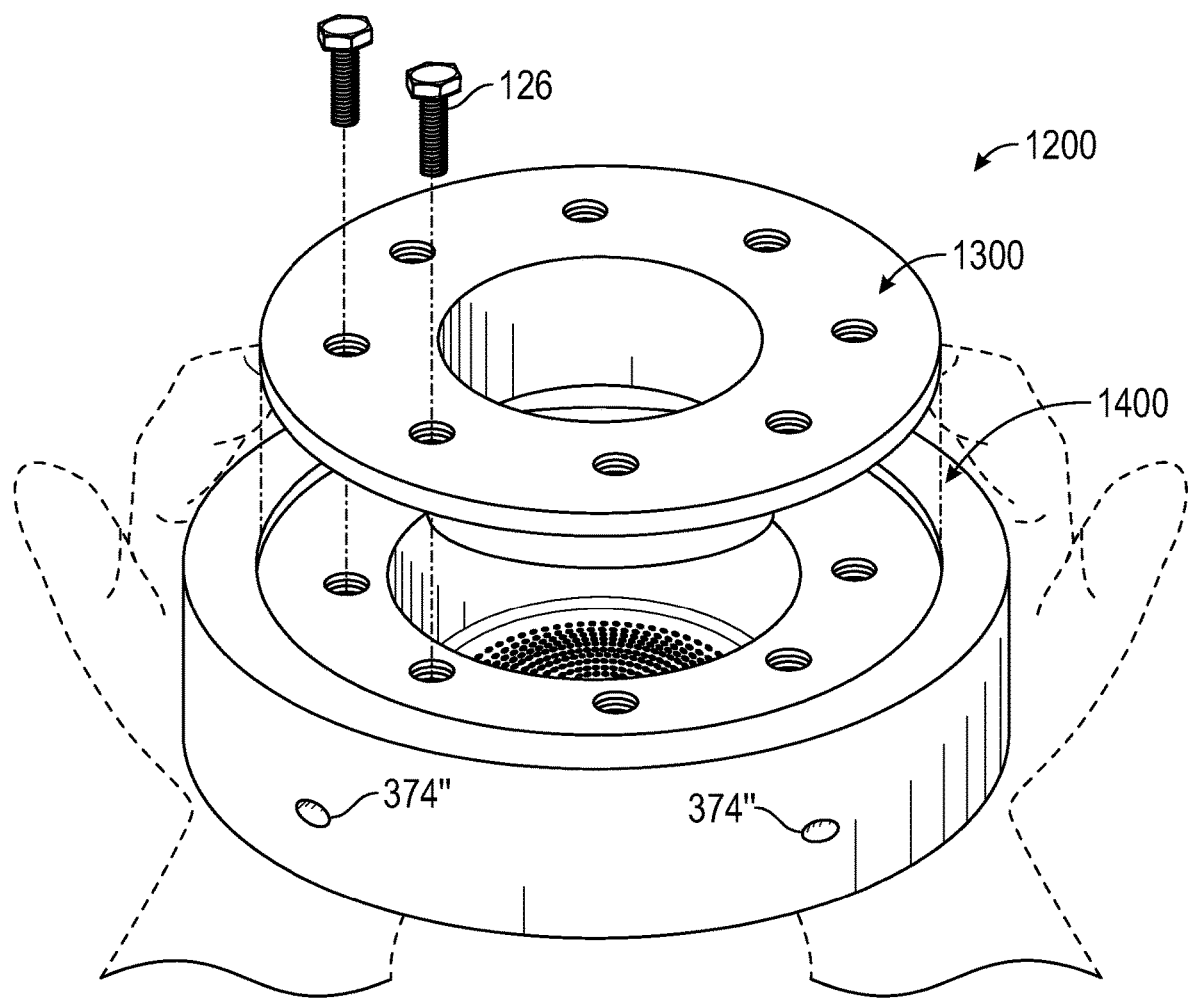
FIG. 15 shows an exploded perspective view of a portion of the embodiment testing apparatus 1200.

FIG. 15 shows an exploded perspective view of the embodiment testing apparatus 1200. According to one or more embodiments, the testing apparatus 1200 may be used for observing the interaction and performance of a treatment fluid on a core sample as part of a core sample assembly. The exploded view of the testing apparatus 1200 shows the top housing 1300 and the base housing relative to one another and how the components couple to form testing apparatus 1200. The optional light connector is not shown from this view; however, its function with the base housing 1400 has been previously described and shown with other embodiments, and such may be applied to testing apparatus 1200. A pair of hands (in relief) to give perspective to a useful size of embodiment testing apparatus 1200; however, as previously stated, embodiment testing apparatuses may be scaled to greater or reduced sizes.

Preparing embodiment testing apparatus 1200 only takes a few steps. The core sample assembly is positioned within the sample recess such that a core sample is directly observable through the sample viewing window. The core sample assembly, such as core sample assembly 601", is introduced into sample recess 1460 of base housing 1400. The core sample assembly is configured to be positioned entirely within sample recess. Lower surface 613" (not shown) of core sample assembly 601" rests on top of sample recess front surface 1461.

The core sample is directly fluidly accessible through a primary fluid distribution hole in base housing. Resultant fluid or slurry from the test may be expelled from the apparatus 1200 using one or more secondary fluid distribution holes 374".

Top housing couples to the front side of the base housing with a fastening means. Top housing 1300 is introduced at least partially into base housing 1400 such at least a portion of the bottom section 1314 is positioned within sample recess 1460. Bottom section back surface 1306a rests on upper surface 609" (not shown) of core sample assembly 601". At the same time, the top section 1313 is positioned either within or above top housing recess 1440, depending on the core sample assembly thickness 664" of the core sample assembly 601". The top housing 1300 is rotated such that fastener holes 1326 are aligned with fastener holes 1426 of base housing. In this embodiment of the testing apparatus, the apparatus is symmetrical; there is no need or requirement for alignment marks, although they may be optionally included. The fasteners 126 are introduced into the fastener holes 1326, 1426 and are tightened down, securing top housing 1300 to base housing 1400 and fixing core sample assembly 601" in sample recess 1460.

With the securing of the fasteners 126, a surface-to-surface contact is made that form surface contacts within embodiments of testing apparatus 1200. In some embodiments of the testing apparatus, top housing 1300 couples with base housing 1400 such that a surface-surface contact is between sample recess front surface 1461 and the lower surface 613" (not shown) of core sample assembly 601". In regard to the seal between sample recess front surface 1461 and the lower surface (not shown) of core sample assembly 601", a fluid-tight seal does not form where primary fluid distribution hole 370" is positioned; however, the lack of a seal at these locations does not compromise external integrity. Other surface-surface contacts may form upon formation of the testing portion of the embodiment testing apparatus.

Optional light connector is coupled to the back side of the base housing with a second fastening means. Although not shown in FIG. 15, to continue the assembly of embodiment testing apparatus 1200, light connector 400" is coupled with base housing 1400, as has been previously described in other embodiments.

Optionally, one or more secondary fluid conduits 122 may be coupled to a secondary fluid distribution hole 374" as previously described. In such embodiments, the testing apparatus 1200 may have supporting connectors to secure one more secondary fluid conduits.

Method of Use of Testing Apparatus

Figure 16:
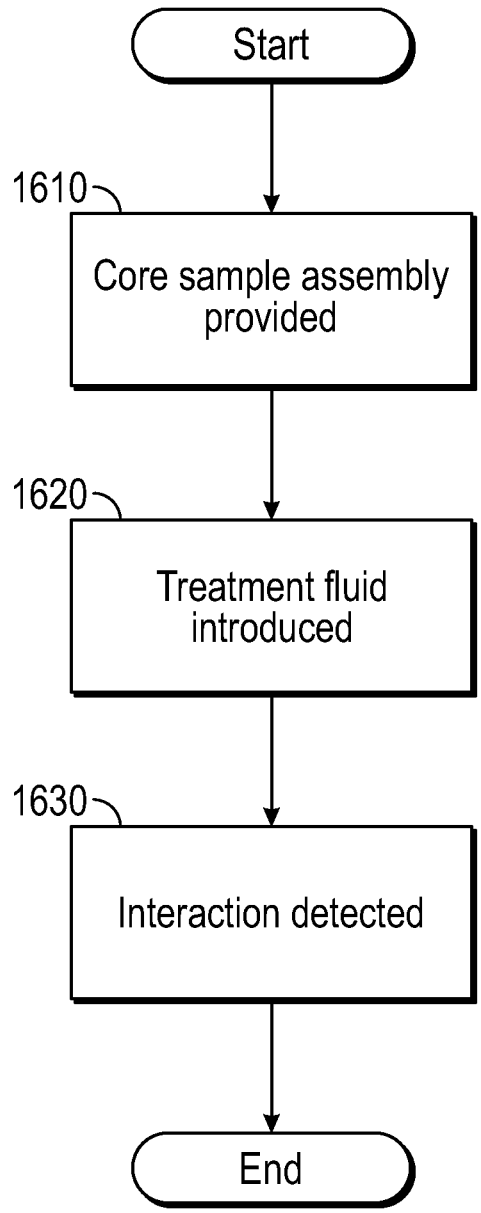
FIG. 16 shows a flowchart of an embodiment method for use with an embodiment testing apparatus, such as the apparatuses described previously and pictured in part or in total in FIGS. 1A-15, and parts thereof.

FIG. 16 shows a flowchart of an embodiment method for use of an embodiment testing apparatus, such as the apparatuses described previously and pictured in FIGS. 1A-15, and parts thereof. While the various steps are represented as a series of blocks and are described sequentially, one of ordinary skill in the art will appreciate that some or all of the steps may be executed in a different order, may be combined, may be omitted, or may be executed in parallel. Furthermore, the steps may be performed actively or passively. The steps may be performed in part or in total by a human, by a machine following pre-written instructions, or both.

For step 1610, a testing apparatus with a core sample assembly having a core sample is provided. For example, an embodiment testing apparatus, such as those previously described as testing apparatus 100, 700, or 1200, may be provided, along with other variants of the testing apparatus. The testing apparatus has a top housing coupled to the front side of the base housing with a fastening means, such as like by fasteners or by the internal/external threading as previously described. Optionally, the light connector is coupled to the back side of the base housing with a second fastening means, for example, the magnetic coupling as previously described, or by other means as can be envisioned by one of ordinary skill in the art.

The testing apparatus is configured with a sample viewing window as previously described. In some embodiments, the viewing window is paneless; in other embodiments, there is a transparent pane, such as a glass or plastic window, present and enclosing sample viewing window.

As previously described for the embodiment testing apparatuses 100, 700, and 1200, the testing apparatus is configured with a sample recess. A core sample assembly is positioned within the sample recess such that the core sample is directly observable through the sample viewing window.

In some embodiments, the core sample assembly is provided. Core sample assembly comprises a core sample to the tested positioned in between an upper surface and a lower surface. The lower surface is configured with a void in the surface to permit fluid to access the core sample though the lower surface. The core sample has a surface finish such that it may form a fluid-tight seal with both the upper surface and the lower surface (except for where the void is present) such that fluid may not bypass the sample in between the respective surfaces and the core sample when pressure is applied to the core sample assembly.

The testing apparatus is also configured as previously described with a primary fluid distribution hole. With the core sample assembly in the sample recess and the primary fluid distribution hole traversing the base housing of the testing apparatus, the core sample is directly fluidly accessible from outside the embodiment testing apparatus, such as through optional light connector or another fluid conduit as previously described. In such a position, the core sample is ready to be tested and observed.

In some configurations of the testing apparatus, such as embodiment testing apparatus 100 and 1200, the sample viewing window is part of the top housing, as previously described. In some other configurations of the testing apparatus, such as embodiment testing apparatus 700, the testing apparatus further comprises a yoke that is coupled to both the top housing and the base housing and is configured with the sample viewing window.

In some other configurations of the testing apparatus, the testing apparatus further comprises at least one secondary fluid distribution hole. In such instances, the core sample assembly is configured such that the core sample is also directly fluidly accessible via the secondary fluid distribution hole(s).

In step 1620, a treatment fluid is introduced into the testing apparatus such that the treatment fluid and the core sample interact. Treatment fluid is introduced into the core sample through the primary fluid distribution hole. As described for some embodiments, the light connector is configured to couple a treatment fluid supply line (previously described as primary fluid conduit 116) to primary fluid distribution hole. Light connector is coupled with base housing such that LC fluid conduit aligns with primary fluid distribution hole and a fluid flow pathway is provided for the treatment fluid to be introduced into the core sample via the void in the lower surface. In some other embodiments, the fluid conduit providing testing fluid into the primary fluid distribution hole is coupled to the base housing on the back surface using a tubing connector or some other means of coupling the fluid supply conduit to the embodiment testing apparatus.

As previously described, the treatment fluid may include one or more various fluids, including gases, liquids, and combinations thereof. In some instances, the treatment fluid may take the form of a slurry; however, the particles should be of an appropriate size to ensure that the core sample fluid flow pathways do not become clogged or otherwise hindered. For example, carbon dioxide may be introduced as a nanosolid in a carrier solution, a gas, a critical fluid, or a supercritical fluid. As another example, the treatment fluid may be introduced at pressures and temperatures ranging from room conditions to simulated formation conditions, including high pressure/high temperature (HPHT) wellbore conditions. In some cases, HPHT may be understood to be wellbore conditions of at least 149° C. and at least 10,000 psi (pounds per square inch), although specifics on the exact definition may vary. In another example, the treatment fluid may contain biologically hazardous components, such as hydrogen sulfide. In such cases, the embodiment testing apparatus is configured to safely handle such conditions and fluids, including by use of appropriate seals, adhesives, and gaskets, as well as materials of construction of fasteners and housings, while permitting live observation and memorialization.

Examples of treatment fluids may include natural and synthetic waters, such as distilled, fresh, desalinated, mineral, organic-loaded, gray, brown, black, brackish, sea, brines, formation, production, and post-industrial processing waters. Treatment fluids may include air and gas products, including, but not limited to, air, "enriched" air, nitrogen, carbon dioxide, carbon monoxide, hydrogen sulfide, noble gases, and combinations thereof. Treatment fluids may include crude oil, natural gas, liquid condensate, other naturally-occurring hydrocarbons, and synthetic and natural fractions thereof, including, but not limited to, methane, ethane, propane, butanes, light petroleum gas (LPG), natural gas lights, naphthas, mineral spirits, mineral oils, kerosenes, "Safra oil" (that is, dearomatized mineral oil and dearomatized kerosene), BTEX (benzene/toluene/ethyl benzene/xylenes), BTX, diesels, atmospheric and vacuum gas oils, vacuum residuals, maltenes, and asphaltenes, and combinations thereof. Treatment fluids may include salts, such as salts of ammonium, sodium, calcium, cesium, zinc, aluminum, magnesium, potassium, strontium, silicates, lithium, iron, and combinations thereof. Treatment fluids may include salts that disassociate to form ions of chlorides, bromides, carbonates, hydroxides, iodides, chlorates, bromates, formats, nitrates, sulfates, phosphates, oxides, fluorides, and combinations thereof. Treatment fluids may include natural and synthetic polymers.

Optionally, treatment fluids may include dyes, tracers, and other additives for permitting or facilitating the visual or sensor detection of the interaction of the treatment fluid with the core sample. For example, a treatment fluid, such as a reactive fluid, such as an acidic fluid, may produce bromine gas as a byproduct of the reaction. When such a reaction proceeds to generate the acid and the bromine gas, the resultant of the treatment fluid interacting with the core sample changes from colorless to orange. This vapor having a reaction product that produces a visible color permits observation and memorialization of the formation of the acid system within the core sample assembly. In some embodiments, the dye or tracer may be light or photo-sensitive such that it reacts upon exposure to light. For example, the dye or tracer may demonstrate fluorescence or phosphorescence upon exposure to electromagnetic (EM) energy, such as through visual or UV spectrum light.

Treatment fluids may include reactive fluids. A reactive fluid is a composition having one or more materials that upon initiating a reaction then react and form a product different than the reactant(s). Forming a product in situ of formation material, such as a core sample or core slice, is of interest. An example of a reactive fluid may include an epoxy thermosetting resin introduced with a curing agent. Introduced of this material into the core sample a reaction may occur where an epoxy thermoset polymer forms in the core sample matrix.

In some embodiments, the reactive fluid is configured to react with the core sample. In some embodiments, the reactive fluid is an acidic fluid. An acidic fluid may include an organic acid. Useful organic acids may include, but are not limited to, alkanesulfonic acids, arylsulfonic acids, formic acid, acetic acid, methanesulfonic acid, p-toluenesulfonic acid, alkyl carboxylic acids, aryl carboxylic acids, lactic acid, glycolic acid, malonic acid, fumaric acid, citric acid, tartaric acid, chloroacetic acid, dichloroacetic acid, trichloroacetic acid, fluoroacetic acid, difluoroacetic acid, trifluoroacetic acid, glutamic acid diacetic acid, methylglycindiacetic acid, 4,5-imidazoledicarboxylic acid, and combinations thereof.

An acidic fluid may include an inorganic acid, also known as mineral acids. Strong acids may include, but are not limited to, hydrochloric acid, (HCl), chloric acid ($HClO_3$), hydrobromic acid (HBr), sulfuric acid ($H_2SO_4$), nitric acid ($HNO_3$), perchloric acid ($HClO_4$), hydroiodic acid (HI), phosphoric acid ($H_3PO_4$), and combinations thereof. Such acids may be introduced as liquid concentrates or as solids that are hydrated within the core sample, or they may be provided as their own solution.

In some other embodiments, the reactive fluid is configured to degrade and form a second reactive fluid in the core sample, where the second reactive fluid is reactive with the core sample. Examples of a first reactive fluid that degrades and forms a second reactive fluid, which in some instances may be an acidic fluid, include hydrolyzable compounds, such as esters or nitrile-containing compounds.

In some other embodiments, the reactive fluid is configured to degrade within the core sample and form a second reactive fluid within the core sample, where the second reactive fluid is reactive with a third reactive fluid that is present in the core sample or is introduced after degradation of the first reactive fluid. In such an instance, the third reactive fluid may not be reactive with the first reactive fluid.

In some embodiments, a first reactive fluid is configured to react with a second reactive fluid present in the core sample. An example of a first reactive fluid reacting with a second reactive fluid may include an epoxy thermosetting resin introduced with a curing agent. Introduction of this mixture into the core sample permits a reaction to occur where an epoxy thermoset polymer forms within the core sample matrix.

Another example of a reactive system is provided. A composition for forming an acidic fluid in situ may include introduction of a first reactive fluid—an aqueous fluid with an acid precursor—with a second reactive fluid—an oxidizing agent configured to oxidize the acid precursor. As used, "in situ acid generation" and variations thereof means that an acid used for dissolving the matrix of the core sample is generated within the core sample from introduced compositions that are acid precursors. This is in contrast to forming an acidic solution and then introducing the acidic solution into the testing apparatus, as previously described.

To provide an example of in situ acid generation, an acid precursor may include an ammonium salt, such as an ammonium halide. The ammonium halide may include, but is not limited to, ammonium fluoride, ammonium chloride, ammonium bromide, ammonium iodide, and combinations thereof. The ammonium salt may also include, but is not limited to, hydrogen difluoride, and a polyatomic anion. Polyatomic anions include, but are not limited to, sulfates, including hydrogen sulfate; thiosulfates; nitrites; nitrates; phosphites; phosphates, including monohydrogen phosphate and dihydrogen phosphate; carbonates; and combinations thereof.

In some embodiments, an ammonium salt may include one or more N-substituted ammonium salts. The N-substituted ammonium salt may be mono-substituted or di-substituted, for instance, with one or two alkyl groups. Tri-N-substituted ammonium salt is tri-substituted with, for example, three alkyl groups. Alkyl groups may include, but are not limited to, methyl, ethyl, propyl, and butyl. In some embodiments, an ammonium salt is not a tri-substituted ammonium salt. In some embodiments, an ammonium salt is not a tetra-substituted ammonium salt.

To continue the example, an oxidizing agent comprises an agent configured to oxidize an ammonium salt. In some embodiments, an oxidizing agent includes an inorganic oxidizer. Further, an oxidizing agent may include an agent selected from the group comprising a peroxide, a persulfate salt, a permanganate salt, a bromate salt, a perbromate salt, a chlorate salt, a perchlorate salt, an iodate salt, a periodate salt, and combinations thereof. In certain embodiments, an oxidizing agent is a bromate salt, such as an alkali bromate salt, such as sodium bromate. In some other embodiments, an oxidizing agent includes an organic oxidizer. In some such embodiments, an oxidizing agent comprises an agent selected from the group comprising peracetic acid, performic acid, and combinations thereof.

In some embodiments, an introduced reactive fluid includes a composition comprises an aqueous fluid having an ammonium salt configured to be oxidized to produce acid and an oxidizing agent configure to oxidize the ammonium salt.

In some embodiments, an ammonium salt and oxidizing agent in an aqueous fluid react to produce an acidic fluid at a temperature equal to or greater than 65° C. In such an instance, the acidic fluid may react with the core sample matrix upon formation, driving the reaction to completion.

In an embodiment, a first reactive fluid is introduced to the core sample through the primary fluid distribution hole. In such an embodiment, a second reactive fluid configured to react with the first reactive fluid is introduced to the core sample through the primary fluid distribution hole. In some certain embodiments, the first reactive fluid and the second reactive fluid may react to form an adduct within the core sample, effectively a third material that is different from the first and second materials. In other such embodiments, the first and the second reactive fluids may mix and dilute one another such that they act in concert on the core sample matrix.

In some certain embodiments, a reactive fluid is configured to disassociate and form a second fluid due to conditions in the core sample, such as pressure or temperature, or due to an interaction with a material within the core sample. Examples of possible materials within the core sample that may disassociate include salt ions and acids.

In some embodiments, the first reactive fluid and the second reactive fluid are both introduced simultaneously through the primary fluid distribution hole. In such instances, the two reactive materials may not react until the fluids reach the conditions of the core sample, such as temperature or pressure.

In some other embodiments, the first reactive fluid and the second reactive fluid are introduced in series through the primary fluid distribution hole. In such an embodiment, there may be perfect or near-perfect mixing of the two reactive materials, or there may be a residual of the first reactive material that remains that is enough to start a reaction between the first and the second reactive material within the core sample. Other variations of reactive fluid interactions within the core sample assembly are envisioned where all the reactive fluids are introduced through primary fluid distribution hole.

The testing apparatus may hold the core sample at various testing conditions, such as from room conditions to simulated downhole conditions, as previously described.

Optionally, where the embodiment testing apparatus is configured to have more than one secondary fluid distribution holes, more options for studying fluid behavior interacting with and within the core sample are feasible. The secondary fluid distribution holes may act as one or more "production wells" in studying formation behavior. In some instances, an effluent fluid or slurry as the resultant from the interaction between the core sample and the treatment fluid forms and is passed into the secondary fluid distribution hole for elimination. Fluid flow may occur between the primary fluid distribution hole and one or more secondary fluid distribution holes. The variations are potentially endless depending on the configuration and number of secondary fluid distribution holes.

In step 1630, the interaction within the testing apparatus between the treatment fluid and the core sample is detected. The testing apparatus may enable detection, observation, and memorialization of the treatment fluid as it flows into and interacts with the core sample in real-time. In some instances, such as the use of a reactive fluid or an acidic fluid, the attenuation of the core sample through reaction may be observed in real-time. "Attenuation" in this use means that the core sample had an original configuration in its matrix, but after the introduction of treatment fluid a chemical or physical reaction occurs within the matrix that transforms the matrix to a new configuration. For example, the formation of wormholes, fluid flow channels, or voids fundamentally changes the configuration of the matrix from a first state to a second state, where the second state has less material comprising the matrix than the first state.

In some embodiments, the detection of the interaction between the treatment fluid and the core sample is through direct visual observation. Visual observation may be made by an observer, such as by a mechanical means, including a lens if the observer is synthetic, through the sample viewing window of the top housing or the yoke. The core sample assembly containing the core sample is positioned within the embodiment testing apparatus.

Optionally, light is transmitted through the core sample assembly and through the core sample such that it may be illuminated. In some embodiments, light is supplied by the light connector, as previously described. Light is transmitted through the one or more light distribution holes formed in the base housing of the embodiment testing apparatus. Light illuminates the core sample and any space around it where light distribution holes are present. During introduction of the treatment fluid, light is also transmitted through the treatment fluid such that it is also illuminated.

If the core sample of the core sample assembly has a thickness that is about or less than 2 mm, in some instances the light from the light connector is sufficient to render at least parts of the core sample semi-translucent. In such instances, it is feasible to view, detect, and memorialize the interaction of the treatment fluid within the interior of the normally opaque core sample. In other instances, external illumination through the sample viewing window may be used, as will be described.

In some instances, as previously described, the treatment fluid may comprise a dye or tracer that is configured to react to electromagnetic radiation (EM), such as fluorescent or phosphorescent materials. Such light-reactive dyes or tracers may assist in detecting aspects of a core sample in real-time. Another example of a useful dye or tracer-type additive may include magnetically responsive material.

In some embodiments, additional illumination sources external to the testing apparatus may be used to illuminate or irradiate the core sample through the sample viewing window. Such electromagnetic (EM) radiation may include, but are not limited to, visible light, infra-red (IR) light, ultra-violet (UV) light, radioactive sources (alpha, beta, gamma particle emitters), sonic emitters, and X-ray emitters. Such additional illumination may reveal other aspects of the treatment fluid interaction with the core sample in real-time. Such interactions may be memorialized using both media that can record visual as well as information that is not visual, such as IR-sensing cameras and computers with programs for detecting and recording IR-information, such that the heat flow within the core sample may be detected as the treatment fluid is introduced into the core sample.

Although the embodiment testing apparatus provides for the ability to visually access the core sample during testing, there are indirect testing methods that may also provide similar if not greater value. In some embodiments, the fluid or slurry flow to and from the device may be monitored to evaluate the interaction within the testing apparatus between the treatment fluid and the core sample. Such detection may include flow volume or mass detection in and out of the testing apparatus, for example, determining the rate of dissolution of a matrix acid by changes in fluid volume or slurry mass passing from a core sample. Another example is detection of the concentration of a specie in the spent treatment fluid or in both the introduced treatment fluid and the spent treatment fluid, such as looking for the appearance of a tracer from a secondary fluid distribution hole. As well, determining the change in concentration of a hydrophilic or hydrophobic component may indicate a determination of wettability ion adsorption rate into a formation sample by the relative change in concentrations between introduction and passing fluids into and out of the testing apparatus. Another example is detecting core sample weight change due to interaction with a treatment fluid, such as due to dissolution of the core sample matrix from acidification or from a liquid being pushed out of the core space by a foam, by tracking the weight of the apparatus during testing and monitoring the density of the fluids introduced. Yet another example would be taking a nuclear magnetic resonance (NMR) or a magnetic shift reading from interaction of the treatment fluid with the core sample. Detecting such treatment fluid and the core sample interactions indirectly while still operating the testing apparatus for other purposes is expected and well appreciated.

Optionally, the interaction within the testing apparatus between the treatment fluid and the core sample is memorialized. Detecting the interaction of the treatment fluid with the cores sample may use various apparatuses, systems, and devices for memorialization, recording and archiving the detected interaction. In some embodiments, the memorialization is optical. For example, a video or still camera may capture a single or a series of images, or collect a continuous moving image, of the interaction between the core sample and the treatment fluid as available through the sample viewing window. Such images may later be analyzed in a variety of ways known to those of skill in the art.

Unless defined otherwise, all technical and scientific terms used have the same meaning as commonly understood by one of ordinary skill in the art to which these systems, apparatuses, methods, processes, and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the apparatus has been described with respect to a limited number of embodiments, those skilled in the art, having the benefit of this disclosure, will appreciate that other embodiments can be devised that do not depart from the scope as described. Accordingly, the scope should be limited only by the accompanying claims.

What is claimed is:

1. A testing apparatus, comprising:
   a top housing coupled to a front side of a base housing configured for a surface-surface contact between the top housing and the base housing,
   a light connector comprising a light source configured to couple to a back side of the base housing and configured for a surface-surface contact between the base housing and the light connector,
   where the testing apparatus is configured with a sample viewing window that is paneless, a sample recess defined by the base housing on the front side,
   a core sample assembly comprising a core sample positioned within the sample recess observable though the sample viewing window, and
   a primary fluid distribution hole defined by the base housing,
      wherein the core sample positioned in the sample recess is fluidly accessible through the primary fluid distribution hole, and
      wherein the core sample assembly positioned in the sample recess while the top housing is coupled to the base housing is secured and immobile, and is configured for a surface-surface contact between a lower surface of the core sample assembly and the front side of the base housing.

2. The testing apparatus of claim 1 where the light connector further comprises light emitting diodes (LEDs).

3. The testing apparatus of claim 1, wherein:
   the base housing defines a light distribution hole, and
   the core sample positioned in the sample recess is illuminated by light transmitted from the light connector through the light distribution hole.

4. The testing apparatus of claim 1, wherein:
   the base housing defines a secondary fluid distribution hole, and
   the core sample positioned in the sample recess is fluidly accessible through the secondary fluid distribution hole.

5. The testing apparatus of claim 1 where the top housing defines the sample viewing window.

6. The testing apparatus of claim 1 where the top housing further comprises external threads, the base housing further comprises internal threads, and the top housing and the base housing couple together through a threaded connection, the threaded connection being a surface-surface contact.

7. The testing apparatus of claim 1 where the light connector further comprises magnets, the base housing further comprises materials subject to magnetism, and the light connector and the base housing couple together through a magnetically induced connection.

8. The testing apparatus of claim 7 where a configuration of the magnets in the light connector and a configuration of materials subject to magnetism are asymmetrically coordinated.

9. The testing apparatus of claim 1 further comprising a yoke, where the yoke is configured to couple to the top housing and configured for a surface-surface contact between the top housing and the yoke, and where the yoke is configured to couple to the base housing and configured for a surface-surface contact between the top housing and the yoke.

10. The testing apparatus of claim 9 where the yoke defines the sample viewing window.

11. The testing apparatus of claim 9 where the yoke forms a surface-surface contact with an upper surface of the core sample assembly.

12. The testing apparatus of claim 9 where the yoke defines a stop gap and the base housing defines a coordinated stop.

13. A method of testing a core sample using a testing apparatus, comprising:
   providing a testing apparatus with a core sample assembly including the core sample, where the testing apparatus has a top housing coupled to a front side of a base housing, where a light connector comprising a light source is coupled to a back side of the base housing, where the testing apparatus is configured with a sample viewing window that is paneless, with a sample recess defined by the base housing on the front side and the core sample assembly comprising a core sample positioned within the sample recess is observable though the sample viewing window, with a primary fluid distribution hole defined by the base housing wherein the core sample is fluidly accessible through the primary fluid distribution hole, and the core sample assembly positioned in the sample recess is secured and immobile, forming a surface-surface contact between a lower surface of the core sample assembly and the front side of the base housing;

introducing a treatment fluid into the testing apparatus;

passing the treatment fluid through the primary fluid distribution hole whereby the treatment fluid interacts with the core sample; and detecting an interaction within the testing apparatus between the treatment fluid and the core sample.

14. The method of claim 13 where the testing apparatus further comprises a secondary fluid distribution hole.

15. The method of claim 13 where the treatment fluid is a reactive fluid.

16. The method of claim 13 where the treatment fluid is an acidic fluid.

17. The method of claim 13 further comprising memorializing the interaction between the treatment fluid and the core sample.

18. The method of claim 13 further comprising: maintaining the core sample at a high-pressure/high-temperature (HPHT) condition during introduction of the treatment fluid.

19. The method of claim 13 further comprising:

transmitting light from the light connector through a light distribution hole in the base housing, and illuminating the core sample.

20. The method of claim 19 where the illuminated core sample is semi-translucent.

* * * * *